(12) United States Patent
Ohlemacher et al.

(10) Patent No.: US 6,613,245 B1
(45) Date of Patent: Sep. 2, 2003

(54) CROSSLINKABLE LIQUID CRYSTALLINE COMPOUNDS

(75) Inventors: Angela Ohlemacher, Schopfheim-Wiechs (DE); Carsten Benecke, Weil am Rhein (DE); Klaus Schmitt, Lörrach (DE)

(73) Assignee: Rolic AG, Zug (CH)

( * ) Notice: Subject to any disclaimer, the term of this patent is extended or adjusted under 35 U.S.C. 154(b) by 0 days.

(21) Appl. No.: 09/744,295

(22) PCT Filed: Jul. 19, 1999

(86) PCT No.: PCT/IB99/01294

§ 371 (c)(1),
(2), (4) Date: Apr. 5, 2001

(87) PCT Pub. No.: WO00/05189

PCT Pub. Date: Feb. 3, 2000

(30) Foreign Application Priority Data

Jul. 24, 1998 (CH) ............................................. 1564/98

(51) Int. Cl.⁷ .............................................. C09K 19/32
(52) U.S. Cl. ............. 252/299.62; 526/245; 252/299.66; 252/299.67
(58) Field of Search .................. 252/299.01–299.7; 526/245

(56) References Cited

U.S. PATENT DOCUMENTS

| | | | |
|---|---|---|---|
| 5,723,066 A | * | 3/1998 | Coates et al. .......... 252/299.01 |
| 5,800,733 A | | 9/1998 | Kelly |
| 5,942,030 A | * | 8/1999 | Schuhmacher et al. ..... 106/493 |
| 6,013,197 A | * | 1/2000 | Parri et al. ............. 252/299.01 |

FOREIGN PATENT DOCUMENTS

| | | |
|---|---|---|
| DE | 44 08 170 | 9/1995 |
| EP | 0331 233 | 9/1989 |
| WO | WO 95/22586 | 8/1995 |
| WO | WO 95/24455 | 9/1995 |

OTHER PUBLICATIONS

Kelly, "Anisotropic Networks," J. Mater. Chem. vol. 5, pp. 2047–2061 (1995).
Derwent Abstract of WO 95/25586.
Derwent Abstract of WO 95/24455.
Derwent Abstract of DE 44 08 170.

* cited by examiner

*Primary Examiner*—Mark F. Huff
*Assistant Examiner*—Jennifer R. Sadula
(74) *Attorney, Agent, or Firm*—Finnegan, Henderson, Farabow, Garrett & Dunner, LLP

(57) ABSTRACT

Compounds of formula (I) wherein A, C and D represent (1) or (2), B represents (3) or (4) wherein at least one of the substituents is other than hydrogen and also at least one of the phenylene rings may be replaced by a 1,4-phenylene ring in which one or two non-adjacent CH groups have been replaced by nitrogen; k, l, m are 0 or 1, wherein k+l+m must be equal to 1 or 2; $Z^1$, $Z^2$, $Z^3$ each independently of the others represents a single bond, $-CH_2CH_2-$, $-CH_2O-$, $-OCH_2-$, $-COO-$, $-OOC-$, $-CH=CH-COO-$, $-OOC-CH=CH-$, $-(CH_2)_4-$, $-O(CH_2)_3-$, $-(CH_2)_3O-$ or $-C\equiv C-$; $R^1$, $R^2$ represent crosslinkable groups, and $S^1$, $S^2$ represent spacer units.

22 Claims, No Drawings

CROSSLINKABLE LIQUID CRYSTALLINE COMPOUNDS

This application is a national stage filing under 35 U.S.C. §371 of international application no. PCT/IB99/01294, filed on Jul. 19, 1999, which published in the English language.

The present invention relates to crosslinkable, especially photocross-linkable, bi-reactive liquid crystalline compounds, to liquid crystalline mixtures comprising such compounds and to the use thereof in the crosslinked state as optical components.

Photocrosslinkable liquid crystals provided with a suitable amount of a photoinitiator can be oriented on a substrate or in a cell by means of suitable orientation layers or in a force field, and can then be crosslinked in that state by irradiation with light of-a suitable wavelength. The resulting structure is retained even at high temperatures. Thus, optical components, such as, for example, waveguides, optical gratings, filters and retarders, piezoelectric cells and cells having non-linear optical (NLO) properties, etc., can be produced. Such optical components can be used, for example, for frequency doubling (SHG) or in colour filters.

Further properties, such as, for example, the birefringence, the refractive index, the transparency, etc., must satisfy different requirements depending on the field of application. For example, materials for optical filters should have high birefringence $\Delta n$ combined with low dispersion $n=f(\lambda)$.

In addition to the general utility of polymerisable i.e. crosslinkable liquid crystals for optical components, such liquid crystalline materials are suitable for cladding glass fibres for optical data transmission. The use of such materials increases the elastic modulus in the longitudinal axis of the fibre, lowers the thermal expansion coefficients and reduces microdistortion losses. This results in increased mechanical stability. Moreover, cross-linkable liquid crystals have an anisotropic thermal conductivity that enables heat to flow in specific directions.

The crosslinkable liquid crystals must have good chemical and thermal stability, good solubility in usual solvents and good stability towards electric fields and electromagnetic radiation. They should have a suitable mesophase in a temperature range from about 25° C. to about +100° C., especially from about 25° C. to about +80° C. It is also important that the components have good miscibility with one another since liquid crystals are generally used in the form of mixtures of several components.

For use in optical retarders, polarisation interference filters (for example Solc filters) etc., it is necessary, in addition, for the optical anisotropy to be as great as possible ($\Delta n=|n_e-n_o|$) while the absorption wavelength is as short as possible., In that manner, the desired optical retardation can be obtained with sufficiently thin LCP films (LCP stands for liquid crystalline polymer).The same applies also to use in cholesteric filters, since the band width of the selective reflection is proportional to the optical anisotropy $\Delta n$.

Conventional photochemically oligomerisable or polymerisable liquid crystals generally have a high melting point and a high clearing point and medium optical anisotropy. Firstly, the high melting point has the disadvantage that during processing spontaneous thermal polymerisation may occur prematurely at just above the melting point. This spontaneous polymerisation leads to the formation of domains, resulting in significant impairment of the optical and thermal properties of the crosslinked layers produced. Secondly, a small temperature difference between the melting point and the clearing point results in a low degree of ordering and thus in a low degree of optical anisotropy. The melting point can be lowered by producing complex mixtures having several components, which enables processing to be carried out at lower temperatures but entails the risk of crystallisation of conventional polymerisable liquid crystals. Photochemically oligomerisable or polymerisable compounds are described, for example, in EP-A-0 331 233.

It is accordingly an object of the present invention to provide oligomerisable or polymerisable i.e. crosslinkable compounds that, on their own or in mixtures, have an optical anisotropy that is as great as possible while the absorption wavelength is as short as possible, especially for use in optical components. They should also have low melting points and high clearing points so that during processing as high a degree of ordering as possible and thus a high degree of optical anisotropy of the LCP film is obtained at just above the melting point. It should further be possible to orient and structure the compounds without domains, and they should also have excellent thermal stability and long-term stability in the crosslinked state. Conventional photochemically oligomerisable or polymerisable liquid crystals generally have only medium optical anisotropy.

The present invention now provides compounds that are outstandingly suitable as individual components or as components of liquid crystal mixtures for the above-mentioned applications.

The present invention relates to compounds of the general formula I:

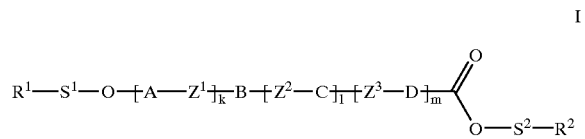

wherein $R^1$, $R^2$ each independently of the other represents a crosslinkable group, such as $CH_2=CH-$, $CH_2=CH-COO-$, $CH_2=C(CH_3)-COO-$, $CH_2=C(Cl)-COO-$, $CH_2=C(Ph)-COO-$, $CH_2=CH-COO-Ph-$, $CH_2=CH-CO-NH-$, $CH_2=C(CH_3)-CONH-$, $CH_2=C(Cl)-CONH-$, $CH_2=C(Ph)-CONH-$, $CH_2=C(COOR')-CH_2-COO-$, $(R'OOC)-CH_2-C=CH_2-COO-$, $CH_2=CH-O-$, $CH_2=CH-OOC-$, $CH=CH-Ph-$, cis- or trans-$-HOO-CR'=CR'-COO-$, siloxane,

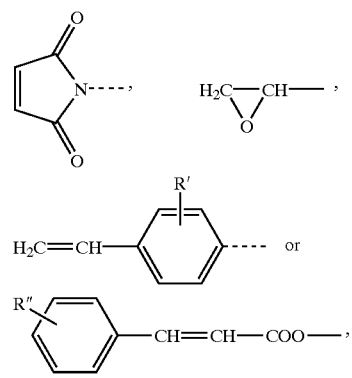

wherein (Ph) represents phenyl, Ph represents phenylene, R' represents lower alkyl and R" represents methyl, methoxy, cyano or halogen;

$S^1$, $S^2$ each independently of the other represents a spacer unit, such as a straight-chain or branched alkylene grouping —$(CH_2)_r$— which may optionally be mono- or poly-substituted by fluorine, or —$((CH_2)_2$—O$)_r$—, or a chain of the formula —$(CH_2)_r$—Y—$(CH_2)_s$— which may optionally be mono- or poly-substituted by fluorine, wherein Y is a single bond or a linking functional group, such as —O—, —COO—, —OOC—, —$NR^3$—, —$NR^3$—CO—, —CO—$NR^3$—, —$NR^3$—COO—, —OCO—$NR^3$—, —$NR^3$—CO—$NR^3$—, —O—OC—O—, —CH=CH—, —C≡C—, wherein $R^3$ represents hydrogen or lower alkyl and r and s are each an integer from 0 to 20, with the proviso that 2≦r+s≦20, or —(Si[$(CH_3)_2$]O)$_u$—, —O$(CH_2)_t$(Si[$(CH_3)_2$]O)$_u$Si[$(CH_3)_2$]$(CH_2)_t$O—, or —NH$(CH_2)_t$(Si[$(CH_3)_2$]O)$_u$Si[$(CH_3)_2$]$(CH_2)_t$NH—, wherein t is an integer from 1 to 12 and u is an integer from 1 to 16, with the proviso that 2t+u≦20;

with the proviso that $R^1$—$S^1$ and $R^2$—$S^2$ do not contain any —O—O— or —N—O— groups;

A, C and D represent

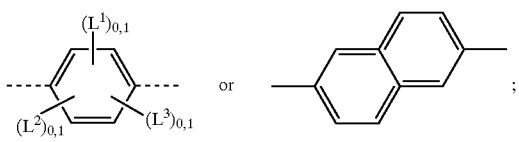

B represents

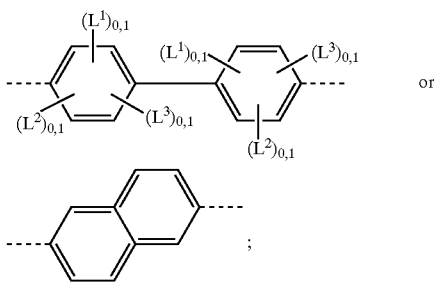

wherein also at least one of the phenylene rings in A, B, C or D may be replaced by a 1,4-phenylene ring in which one or two non-adjacent CH groups have been replaced by nitrogen; and $L^1$, $L^2$, $L^3$ each independently of the others represent hydrogen, $C_1$–$C_{20}$-allyl, $C_2$–$C_{20}$-alkenyl, $C_1$–$C_{20}$-alkoxy, $C_2$–$C_{20}$-alkenylpxy, $C_1$–$C_{20}$-alkoxycarbonyl, formyl, $C_1$–$C_{20}$-alkylcarbonyl, $C_1$–$C_{20}$-alkylcarbonyloxy or nitro, with the proviso that in at least one phenylene ring in A, B, C or D one of the mentioned substituents is other than hydrogen;

k, l, m are 0 or 1, wherein k+l+m must be equal to 1 or 2; and $Z^1$, $Z^2$, $Z^3$ each independently of the others represents a single bond, —$CH_2CH_2$—, —$CH_2O$—, —$OCH_2$—, —COO—, —OOC—, —CH=CH—COO—, —OOC—CH=CH—, —$(CH_2)_4$—, —O$(CH_2)_3$—, —$(CH_2)_3$O— or —C≡C—.

In the structural formulae of the present Application, broken lines ( - - - or —) are used to denote linkages with the adjacent element by a single bond.

Where necessary, the above-used terms will be explained hereinafter.

"Halogen" embraces, in the context of the present invention, fluorine, chlorine, bromine, iodine, especially fluorine and chlorine.

"Lower alkyl" represents, in the context of the present invention, a straight-chain or branched alkyl group having from 1 to 4 carbon atoms, such as, for example, methyl, ethyl, propyl, butyl, isopropyl, isobutyl, tert-butyl, but especially methyl, ethyl, propyl or butyl.

The terms $C_1$–$C_{20}$-alkyl, $C_1$–$C_{20}$-alkoxy, $C_1$–$C_{20}$-alkoxycarbonyl, $C_1$–$C_{20}$-alkylcarbonyl, $C_1$–$C_{20}$-alkylcarbonyloxy embrace, in the context of the present invention, straight-chain or branched saturated hydrocarbon radicals having up to 20 carbon atoms, such as, for example, methyl, ethyl, propyl, butyl, hexyl, heptyl, octyl, nonyl, decyl, undecyl, dodecyl, methyloxy, ethyloxy, n-propiloxy, isopropyloxy, butyloxy, pentyloxy, hexyloxy, heptyloxy, octyloxy, nonyloxy, decyloxy, undecyloxy, dodecyloxy, methoxycarbonyl, ethoxycarbonyl, propoxycarbonyl, butoxycarbonyl, pentyloxycarbonyl, hexyloxycarbonyl, octyloxycarbonyl, nonyloxycarbonyl, decyloxycarbonyl, undecyloxycarbonyl, dodecyloxycarbonyl, methylcarbonyl, ethylcarbonyl, propylcarbonyl, butylcarbonyl, pentylcarbonyl, hexylcarbonyl, octylcarbonyl, nonylcarbonyl, decylcarbonyl, undecylcarbonyl, dodecylcarbonyl, methylcarbonyloxy, ethylcarbonyloxy, propylcarbonyloxy, butylcarbonyloxy, pentylcarbonyloxy, hexylcarbonyloxy, octylcarbonyloxy, nonylcarbonyloxy, decylcarbonyloxy, undecylcarbonyloxy, dodecylcarbonyloxy, and the like.

The terms $C_2$–$C_{20}$-alkenyl and $C_2$–$C_{20}$-alkenyloxy embraces, in the context of the present invention, alkenyl groups having from 2 to 20 carbon atoms, such as 2-alkenyl, 3-alkenyl, 4-alkenyl and alkenyl having a terminal double bond, such as, for example, allyl, 3-butenyl, 4-pentenyl, 5-hexenyl, 6-heptenyl, 7-octenyl, 8-nonenyl, 9-decenyl, 10-undecenyl, allyloxy, 3-butenyloxy, 4-pentenyloxy, 5-hexenyloxy, 6-heptenyloxy, 7-octenyloxy, 8-nonenyloxy, 9-decenyloxy, 10-undecenyloxy and the like.

When any of $L^1$, $L^2$, $L^3$ represents $C_2$–$C_{20}$-alkenyloxy, it may either be a polymerisable group wherein the carbon atom bearing a double bond is directly linked to the oxygen atom, i.e. with the double bond in the 1-position; or a $C_3$–$C_{20}$-alkenyloxy group, wherein the carbon atom bearing a double bond is not directly linked to the oxygen atom.

Such compounds have a surprisingly high degree of optical anisotropy (Δn). Moreover, as components in suitable mixtures they bring about good orientability on orientation layers, which is important, for example, for good contrast.

Preferred compounds of formula I are compounds of formulae I-A to I-G

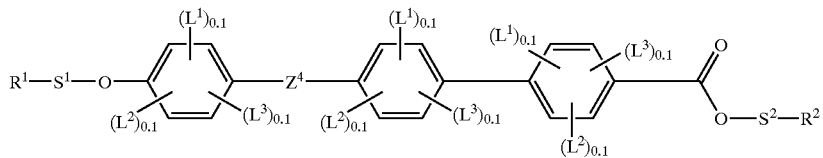
I-A
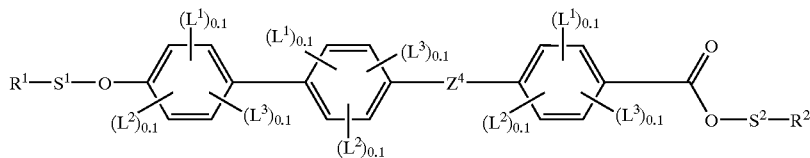
I-B
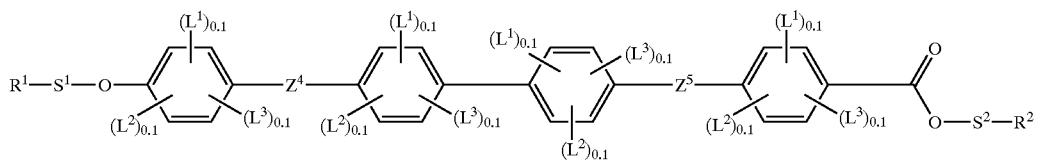
I-C
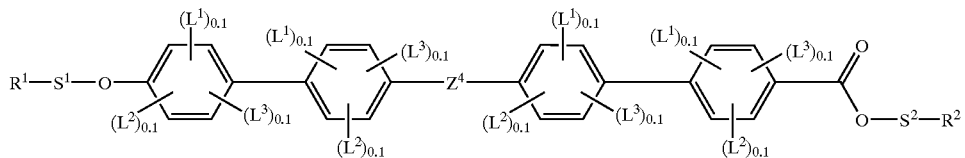
I-D
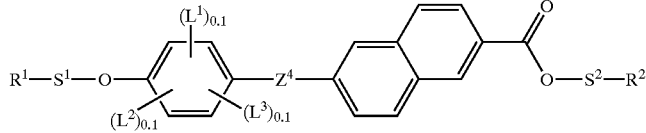
I-E
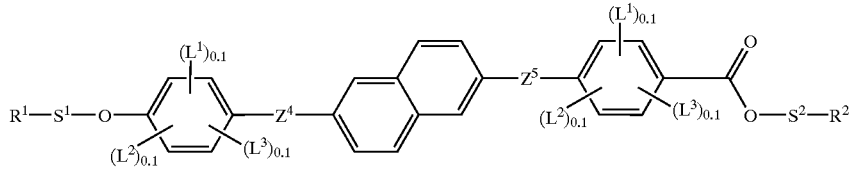
I-F
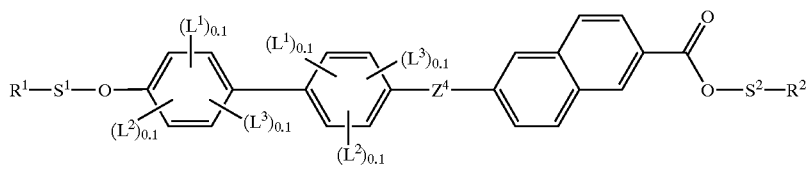
I-G
wherein
$Z^4$, $Z^5$ each independently of the other represents a single bond, —C≡C—, —COO— or —CH=CH—COO—; and
$R^1$, $R^2$, $S^1$, $S^2$, $L^1$, $L^2$ and $L^3$ are as defined for formula I.
Special preference is given to the compounds of formulae I-A, I-B, I-D, I-F and I-G.
Of the compounds of formula I-A, special preference is given to the compounds of formulae I-A-1 and I-A-2
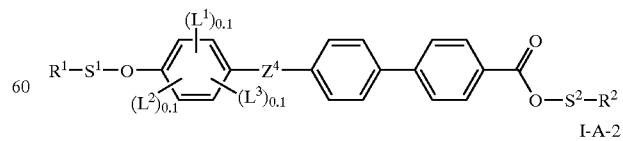
I-A-1
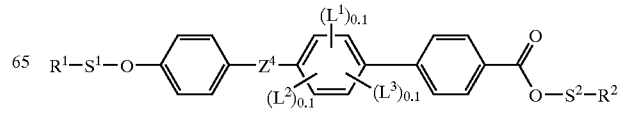
I-A-2 wherein

L$^1$, L$^2$, L$^3$ each independently of the others represents hydrogen, C$_1$–C$_{20}$-alkyl, C$_2$–C$_{20}$-alkenyl, C$_1$–C$_{20}$-alkoxy or C$_2$–C$_{20}$-alkenyloxy, wherein at least one substituent must be other than hydrogen;

Z$^4$ represents —C≡C—, —COO—, —CH=CH—COO—, especially —COO— or —CH=CH—COO—, more especially —COO—; and R$^1$, R$^2$, S$^1$, S$^2$ are as defined for formula I.

Of the compounds of formula I-B, special preference is given to the compounds of formula I-B-1

I-B-1

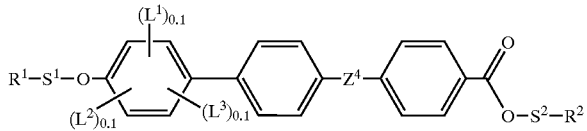

wherein

R$^1$, R$^2$, S$^1$, S$^2$, Z$^4$, L$^1$, L$^2$, L$^3$ are as defined for formula I-A-1.

Of the compounds of formula I-D, special preference is given to the compounds of formulae I-D-1 and I-D-2:

I-D-1

I-D-2

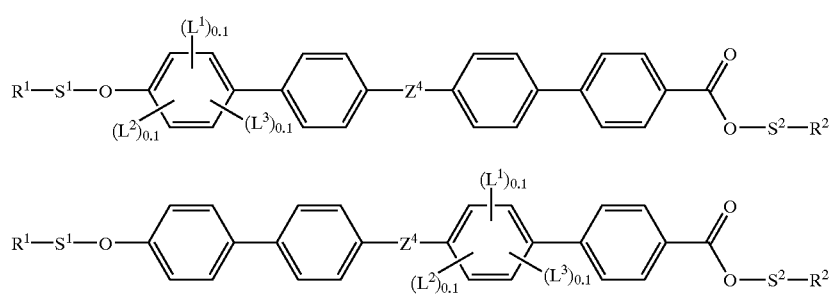

wherein

R$^1$, R$^2$, Z$^4$, L$^1$, L$^2$, L$^3$ are as defined for formula I-A-1.

Of the compounds of formula I-F, special preference is given to the compounds of formula I-F-1

I-F-1

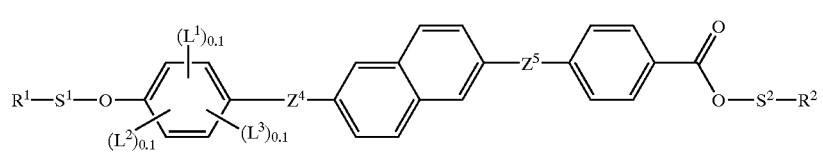

wherein

Z$^5$ represents a single bond, —COO— or —CH=CH—COO—, especially a single bond; and R$^1$, R$^2$, Z$^4$, L$^1$, L$^2$, L$^3$ are as defined for formula I-A-1.

Of the compounds of formula I-G, special preference is given to the compounds of formula I-G-1

I-G-1

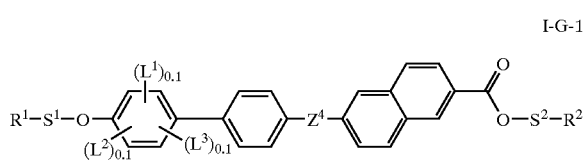

wherein

R$^1$, R$^2$, Z$^4$, L$^1$, L$^2$, L$^3$ are as defined for formula I-A-1.

More especially preferred compounds of formulae I-A-1, I-A-2, I-B-1, I-D-1, I-D-2, I-F-1 and I-G-1 are those wherein the group

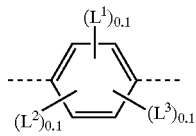

is defined by

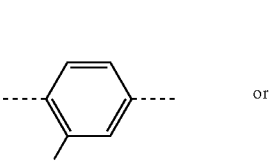 or 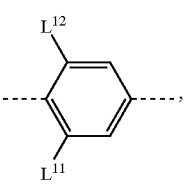

wherein $L^{11}$, $L^{12}$ each independently of the other represents $C_1$–$C_{20}$-alkyl, $C_2$–$C_{20}$-alkenyl, $C_1$–$C_{20}$-alkoxy or $C_2$–$C_{20}$-alkenyloxy, especially $C_1$–$C_{12}$-alkoxy.

The compounds of formula I according to the invention are very easy to obtain synthetically. They can be prepared, for example, analogously to the methods shown in the following Schemes in a manner known per se.

The following abbreviations are used:

DCM dichloromethane

DME dimethoxyethane

DMSO dimethyl sulphoxide

THF tetrahydrofuran

EDC N-(3-dimethylaminopropyl)-N'-ethylcarbodiimide hydrochloride

DEAD azodicarboxylic acid diethyl ester (diethyl azodicarboxylate)

DMAP 4-(dirnethylamino)pyridine

TPP triphenylphosphine

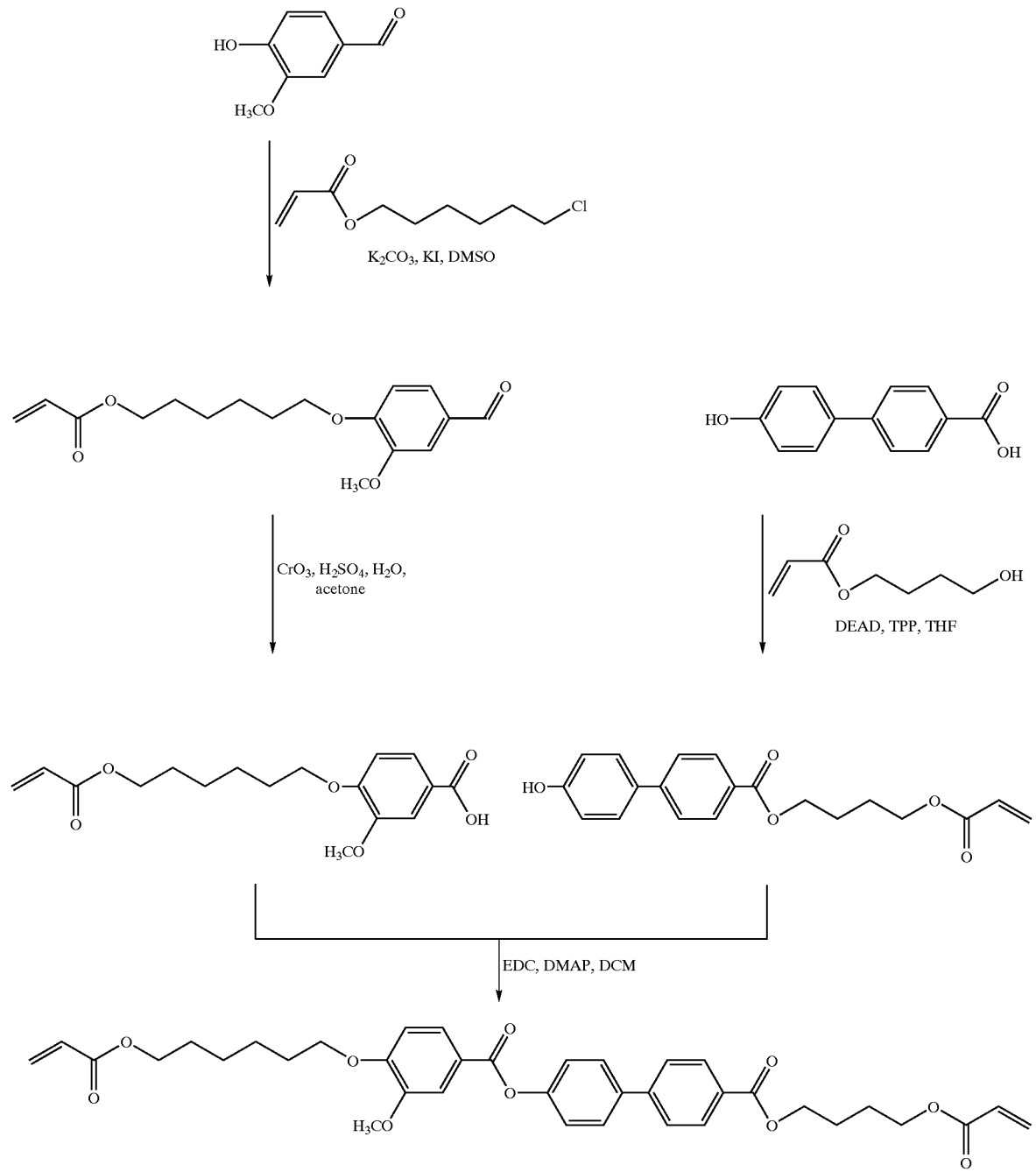

Scheme 1

Scheme 2
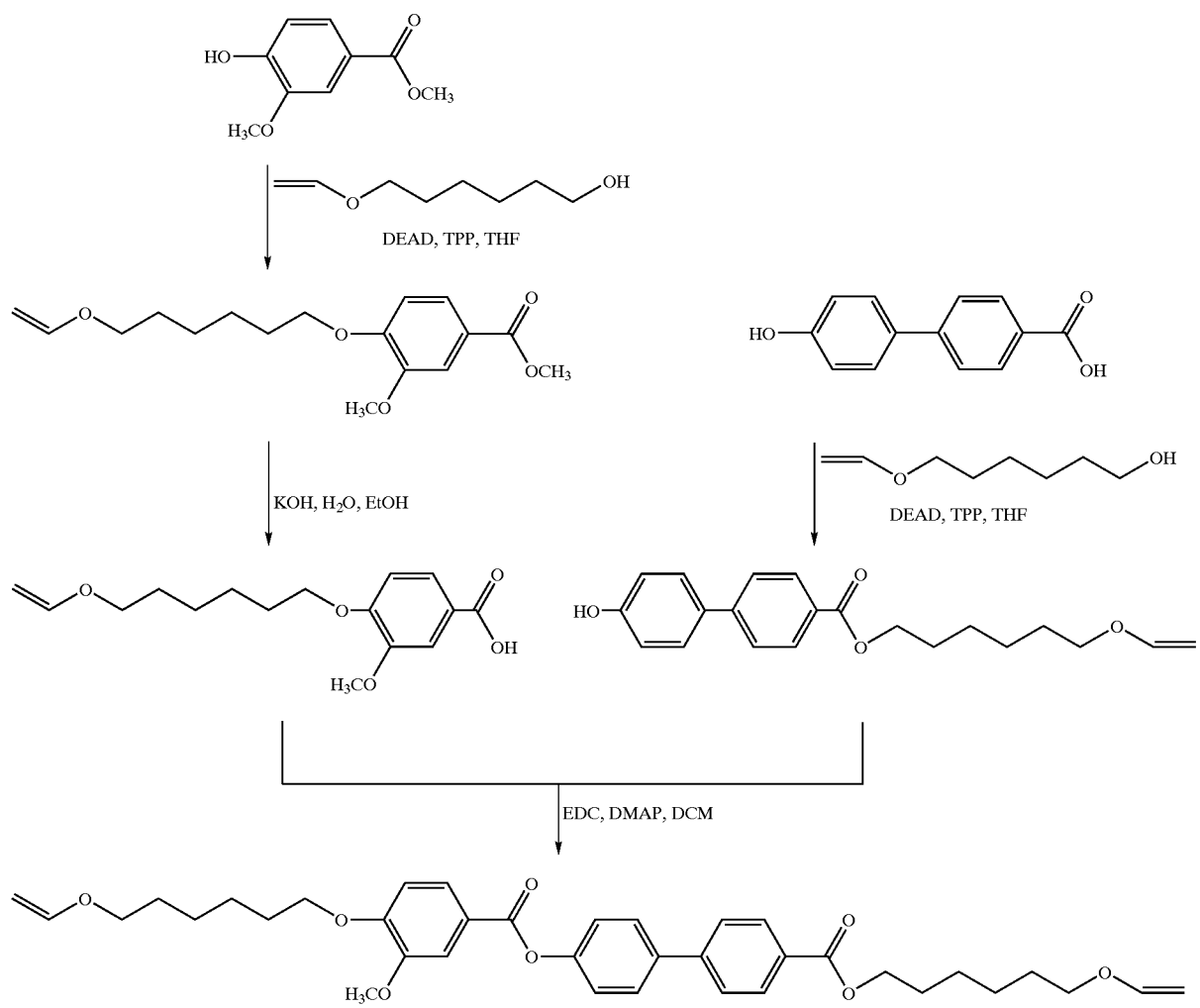
Scheme 3
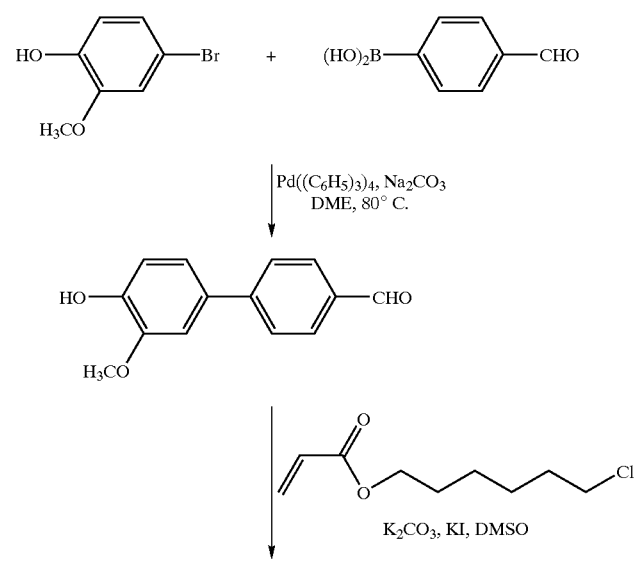

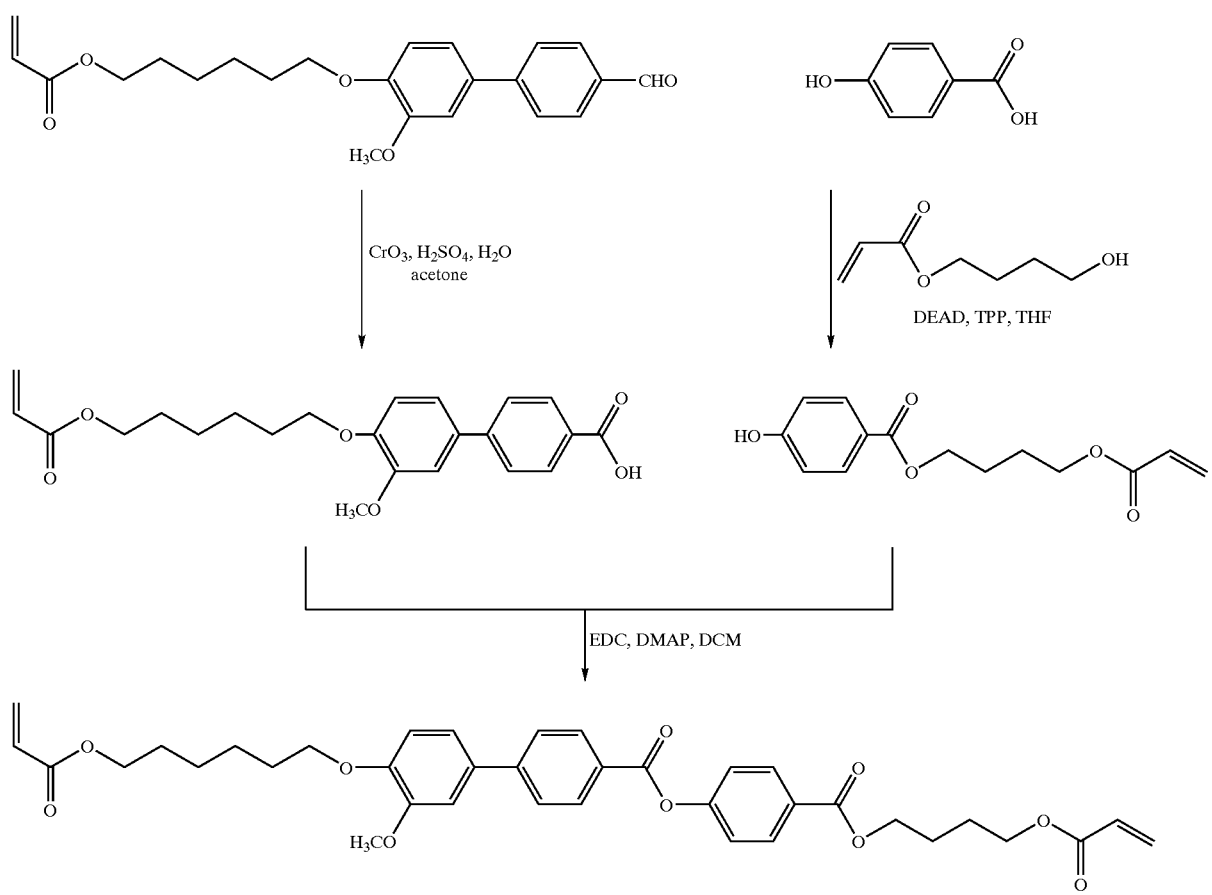
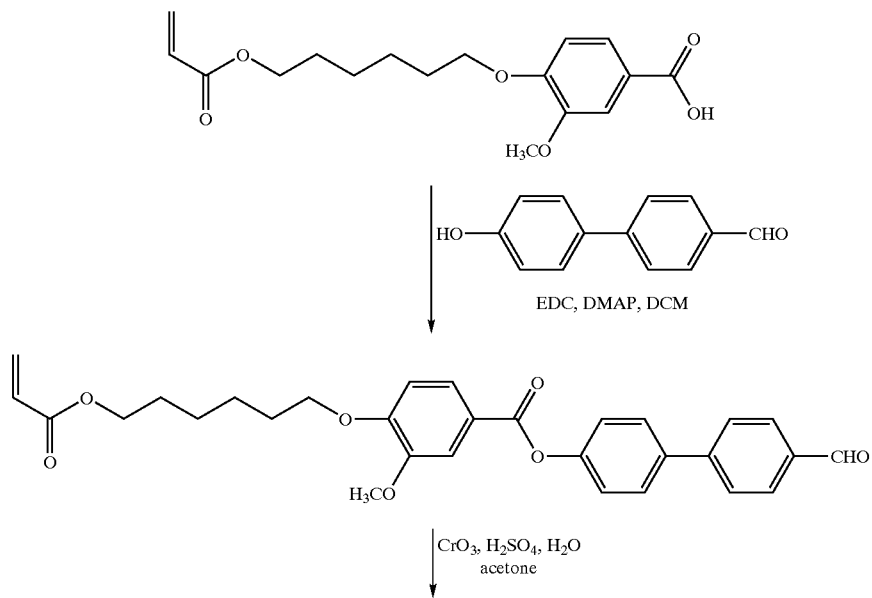
Scheme 4

-continued
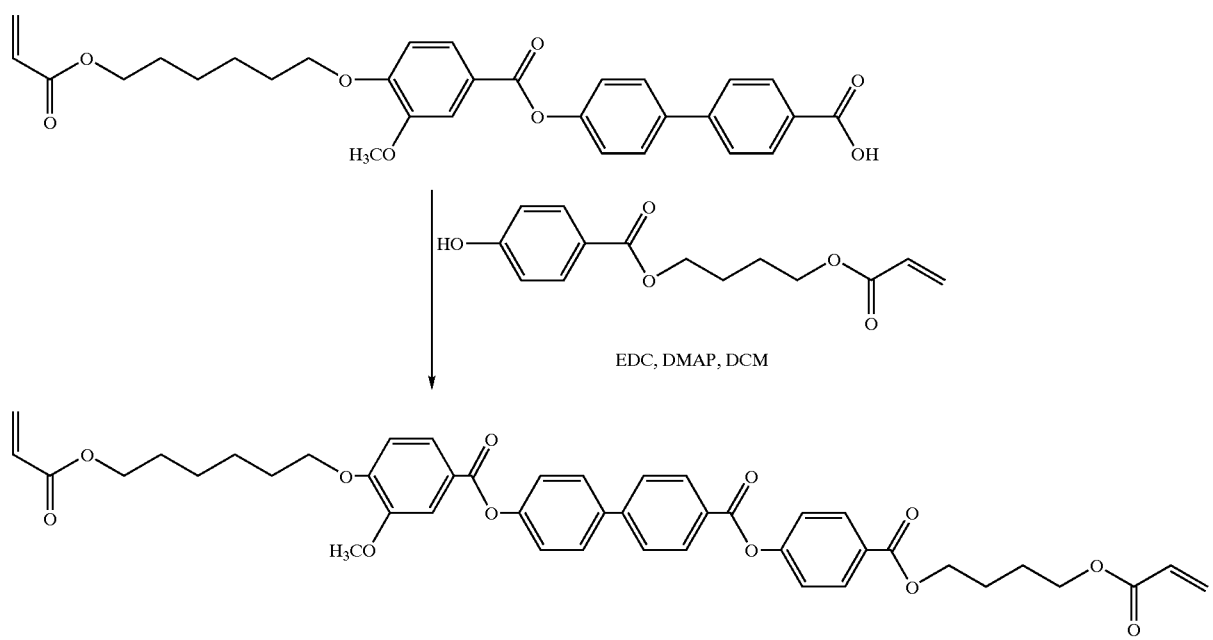
Scheme 5
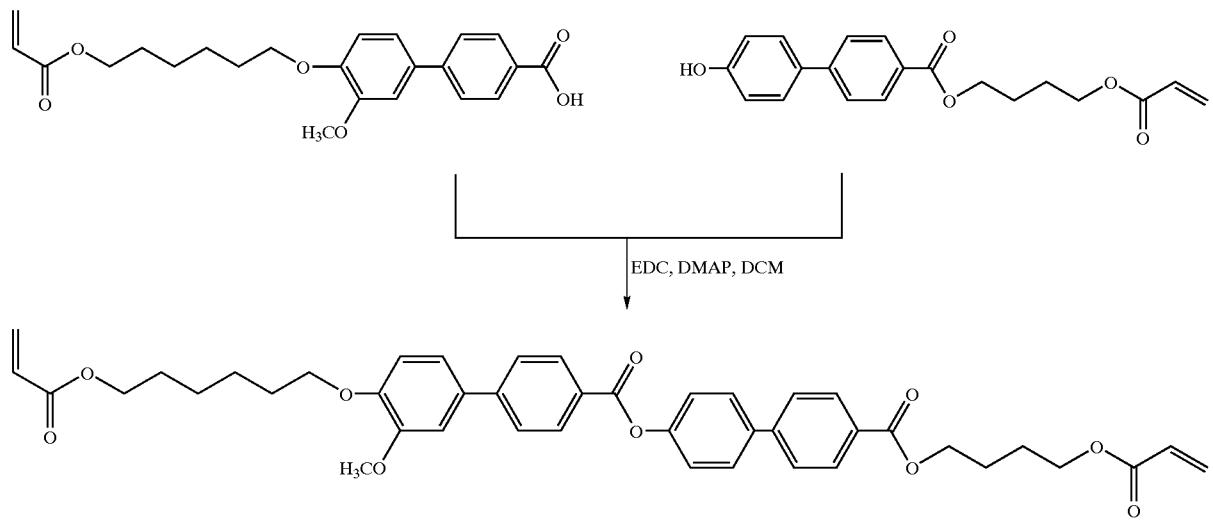
Scheme 6
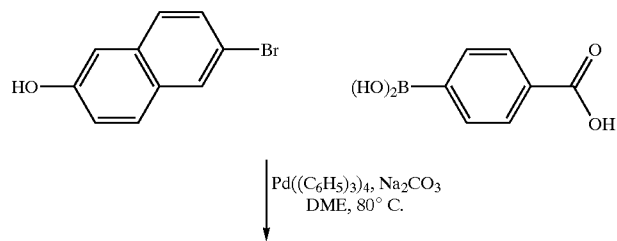

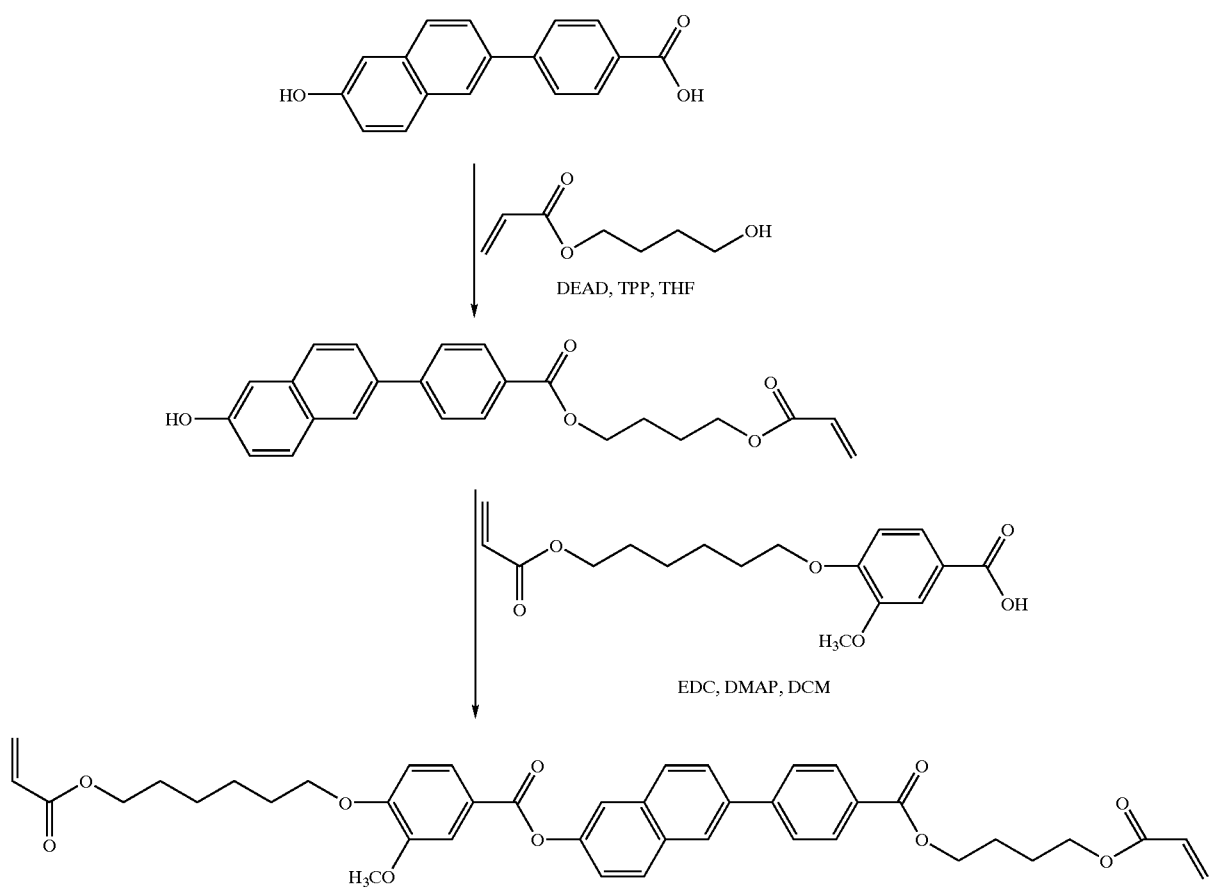
Scheme 7
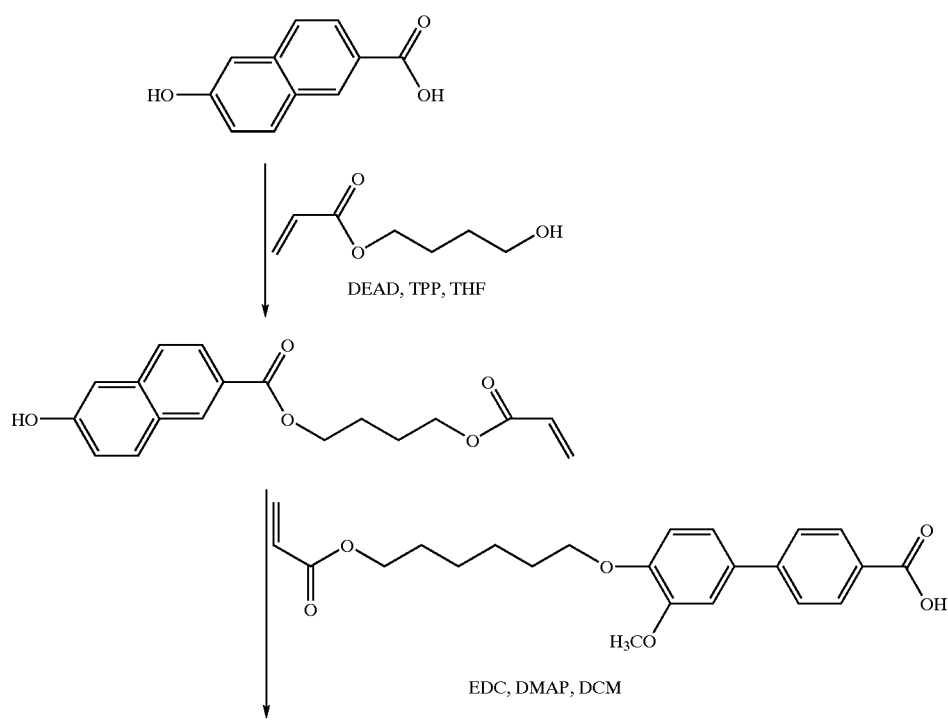

-continued

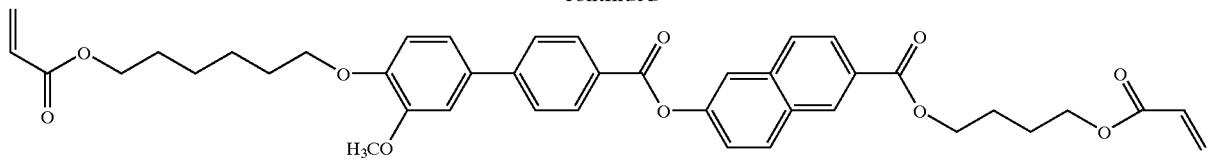

The compounds of formulae I can be used as pure compounds or in the form of mixtures with one another and/or with other liquid crystal components.

The liquid crystalline mixtures according to the invention comprise at least 2 components, of which at least one component is a compound of formula I. A second component and any further components may be further compounds of formula I or other, known liquid crystalline compounds which may have one or more crosslinkable groups. The mixture may also comprise one or more chiral components or isotropic doping agents.

By virtue of the good solubility of the compounds of formula I and by virtue of their good miscibility with one another, the proportion of compounds of formula I in the mixtures according to the invention may be high and may be up to 99% by weight.

The mixtures according to the invention preferably comprise, in addition to one or more compounds of formula I, one or more compounds from the group of compounds of the general formulae

II

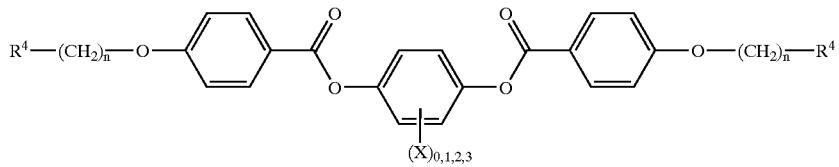

III

IV

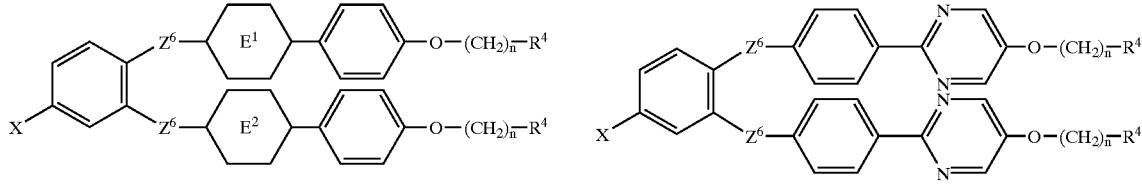

V

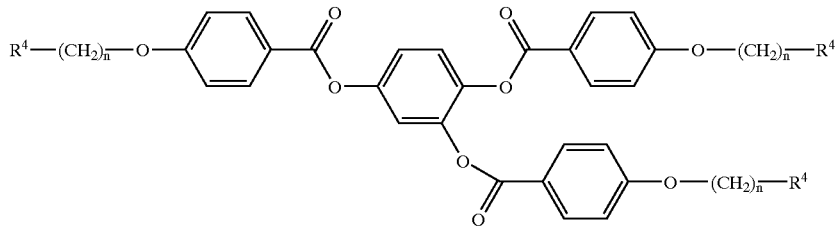

VI

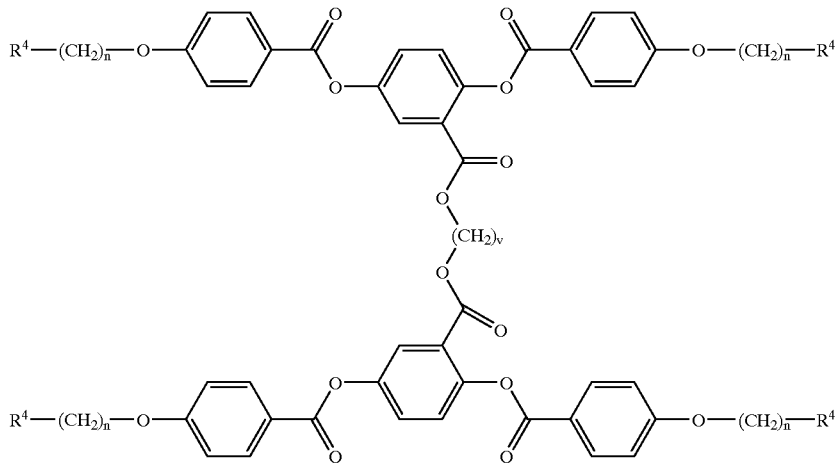

-continued

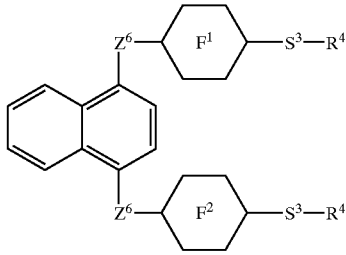
VII

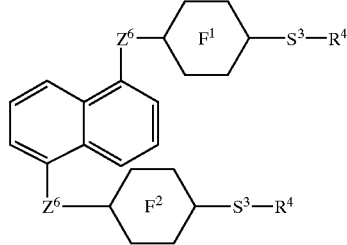
VIII

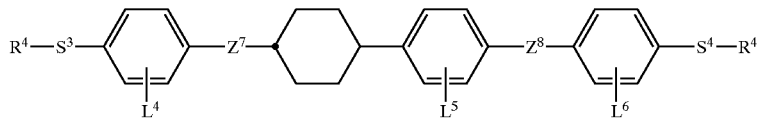
IX wherein

R$^4$ represents a polymerisable group, such as CH$_2$=CH—, CH$_2$=CH—O—, CH$_2$=CH—COO—, CH$_2$=C(CH$_3$)—COO—, CH$_2$=C(Cl)—COO— or

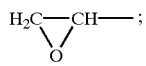

S$^3$, S$^4$ each independently of the other is —(CH$_2$)$_n$— or —O(CH$_2$)$_n$—;

E$^1$, E$^2$ each independently of the other represents 1,4-phenylene, trans-1,4-cyclohexylene, pyridine-2,5-diyl, pyrimidine-2,5-diyl or trans-1,4-cyclohexylene-1,4-phenylene;

F$^1$, F$^2$ each independently of the other represents 1,4-phenylene or 2- or 3-fluoro-1,4-phenylene;

L$^4$, L$^5$, L$^6$ each independently of the others represents hydrogen, C$_1$–C$_{20}$-alkyl, C$_2$–C$_{20}$-alkenyl, C$_1$–C$_{20}$-alkoxy, C$_1$–C$_{20}$-alkoxy-carbonyl, formyl, C$_1$–C$_{20}$-alkylcarbonyl, C$_1$–C$_{20}$-alkylcarbonyloxy, halogen, cyano or nitro;

Z$^6$ represents —COO—, —OOC—, —OCH$_2$—, —CH$_2$O—, —O(CH$_2$)$_3$—, —OOC(CH$_2$)$_2$— or —COO(CH$_2$)$_3$—;

Z$^7$ represents a single bond, —CH$_2$CH$_2$—, —CH$_2$O—, —OCH$_2$—, —COO—, —OOC—, —(CH$_2$)$_4$—, —(CH$_2$)$_3$—, —(CH$_2$)$_3$— or —C≡C—;

Z$^8$ represents a single bond, —CH$_2$CH$_2$—, —CH$_2$O—, —OCH$_2$—, —COO—, —OOC— or —C≡C—;

each X independently of any other(s) represents hydrogen, C$_1$–C$_{20}$-alkyl, C$_2$–C$_{20}$-alkenyl, C$_1$–C$_{20}$-alkoxy, C$_1$–C$_{20}$-alkoxycarbonyl, formyl, C$_1$–C$_{20}$-alkylcarbonyl, C$_1$–C$_{20}$-alkylcarbonyloxy, fluorine, chlorine, bromine, cyano or nitro;

n is an integer from 2 to 20; and v is an integer from 2 to 12.

The preparation of the compounds of formula I and liquid crystalline mixtures comprising those compounds is illustrated further by the following Examples. In the Examples, C represents a crystalline phase, N represents a nematic phase, S represents a smectic phase and I represents the isotropic phase.

EXAMPLE 1

4'-[4-(6-Acryloyloxyhexyloxy)-3-methoxybenzoyloxy]biphenyl-4-carboxylic Acid 4-Acryloyloxybutyl Ester

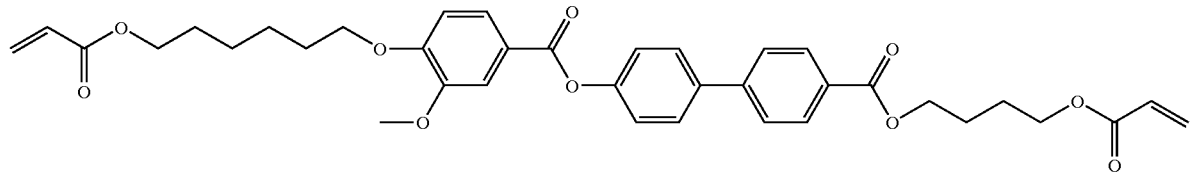

1.35 g (7 mmol) of N-(3-dimethylaminopropyl)-N'-ethylcarbodiimide hydrochloride (EDC) are added at 0° C. to a solution of 2.38 g (7 mmol) of 4'-hydroxybiphenyl-4-carboxylic acid 4-acryloylbutyl ester, 2.26 g (7 mmol) of 4-(6-acryloyloxyhexyloxy)-3-methoxybenzoic acid and 0.86 g (7 mmol) of 4-dimethylaminopyridine (DMAP) in 180 ml of dichloromethane (DCM). The mixture is stirred for one hour at 0° C. and then overnight at room temperature. The reaction mixture is then poured into 300 ml of water and extracted three times with 150 ml of DCM each time. The combined organic phases are washed twice with 200 ml of water each time, dried over magnesium sulphate, filtered and concentrated. Purification of the residue by chromatography on 300 g of silica gel using cyclohexane/ethyl acetate 7:3 and recrystallisation once from 20 ml of ethanol at 0° C. yields 2.58 g of 4'-[4-(6-acryloyloxyhexyloxy)-3-methoxybenzoyloxy]biphenyl-4-carboxylic acid 4-acryloyloxybutyl ester.

M.p. (C—S$_X$) 77° C., S$_X$—N 60° C., Cl. p. (N—I) 62° C.

The 4'-hydroxybiphenyl4-carboxylic acid 4-acryloylbutyl ester used as starting material is prepared as follows:

(a) 5.24 g (20 mmol) of triphenylphosphine (TPP) are added at 0° C. to a solution of 4.28 g (20 mmol) of 4'-hydroxyl-4-biphenylcarboxylic acid and 2.88 g (29 mmol) of 4-hydroxybutyl acrylate in 100 ml of tetrahydrofuran (THF) and then, at the same temperature, 3.50 g (20 mmol) of diethyl azodicarboxylate (DEAD) are added dropwise thereto. The mixture is stirred for one hour at 0° C. and then overnight at room temperature. The mixture is then concentrated and the residue is purified by chromatography on silica gel using cyclohexane/ethyl acetate 2:1 to obtain 4.32 g of 4'-hydroxy-biphenyl-4-carboxylic acid 4-acryloylbutyl ester.

The 4-(6-acryloyloxyhexyloxy)-3-methoxybenzoic acid used as starting material is prepared as follows:

(a) 41.45 g (300 mmol) of potassium carbonate and 27.4 g (165 mmol) of potassium iodide are added to a solution of 22.8 g (150 mmol) of vanillin and 30.7 g (225 mmol) of 6-chlorohexanol in 500 ml of dimethyl sulphoxide (DMSO) and the mixture is stirred overnight at 60° C. under nitrogen. The mixture is then cooled to room temperature, poured into 600 ml of water and extracted three times with 150 ml of ethyl acetate each time. The combined organic phases are washed twice with 200 ml of water each time, dried over magnesium sulphate, filtered and concentrated. Purification of the residue by chromatography on 400 g of silica gel using cyclohexane/ethyl acetate 1:1 yields 29.95 g of 4-(6-hexyloxy)-3-methoxybenzaldehyde.

(b) A solution of 97 ml of Jones' reagent is slowly added dropwise at 5° C. with ice-cooling to a solution of 27.3 g (89.1 mmol) of 4-(6-hexyloxy)-3-methoxybenzaldehyde in 300 ml of acetone. The mixture is then stirred at room temperature for 2 hours. As soon as the starting material can no longer be detected, the reaction solution is poured into 1 litre of water and 0.3 litre of ethyl acetate. The phases are separated and the aqueous phase is extracted twice with 150 ml of ethyl acetate each time. The combined organic phases are washed with 0.5 litre of water, dried over magnesium sulphate, filtered and concentrated. Purification of the residue by chromatography on silica gel using cyclohexane/ethyl acetate 1:1 and recrystallisation once from ethyl acetate/ether yields 16.7 g of 4-(6-acryloyloxyhexyloxy)-3-methoxy-benzoic acid.

Using the appropriate starting compounds, the corresponding compounds are prepared analogously, as shown in Scheme 2, in accordance with reactions known to the person skilled in the art, with vinyl ether as reactive group. Liquid crystals having two different reactive groups can also be synthesised in accordance with the reaction schemes shown.

The following compounds can be prepared in analogous manner:

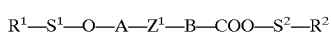

$R^1$—$S^1$—O—A—$Z^1$—B—COO—$S^2$—$R^2$

| $R^1$ | $S^1$—O | A—$Z^1$ | B | COO—$S^2$—$R^2$ | Phase transitions |
|---|---|---|---|---|---|
| acrylate | $(CH_2)_6O$ | methoxy-benzoate | biphenyl | —COO—$(CH_2)_4$—O—acrylate | M.p. (C-1) 79° C. |
| acrylate | $(CH_2)_8O$ | dimethoxy-benzoate | biphenyl | —COO—$(CH_2)_4$—O—acrylate | |
| acrylate | $(CH_2)_7O$ | diethoxy-benzoate | biphenyl | —COO—$(CH_2)_4$—O—acrylate | |
| acrylate | $(CH_2)_6O$ | methyl-benzoate | biphenyl | —COO—$(CH_2)_6$—O—acrylate | |

-continued

| R¹ | S¹—O | A—Z¹ | B | COO—S²—R² | Phase transitions |
|---|---|---|---|---|---|

-continued

| $R^1$ | $S^1$—O | A—$Z^1$ | B | COO—$S^2$—$R^2$ | Phase transitions |
|---|---|---|---|---|---|

-continued
| R¹ | S¹—O | A—Z¹ | B | COO—S²—R² | Phase transitions |
|---|---|---|---|---|---|
| 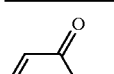 | (CH₂)₆O | 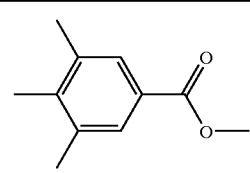 | 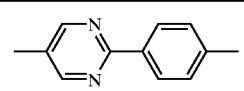 | 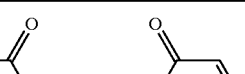 | |
| 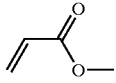 | (CH₂)₇O | 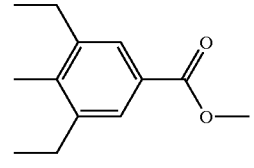 | 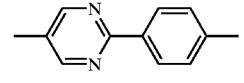 | 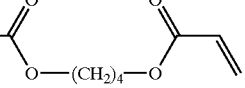 | |
| 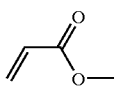 | (CH₂)₆O | 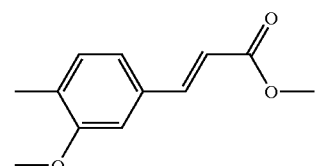 | 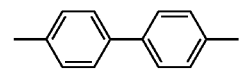 | 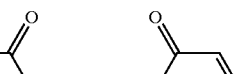 | M.p. (C—N) 95° C., N—I 102° C. |
| 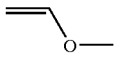 | (CH₂)₆O | 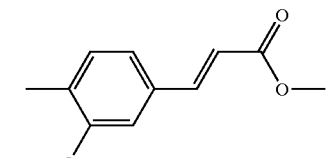 | 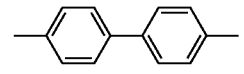 | 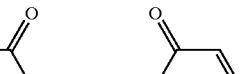 | |
| 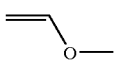 | (CH₂)₆O | 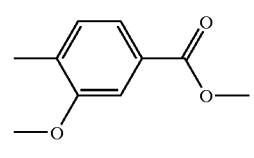 | 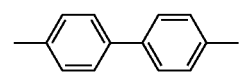 |  | M.p. (C—S_A) 72° C., S_A—I 81° C. |
| 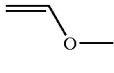 | (CH₂)₆O | 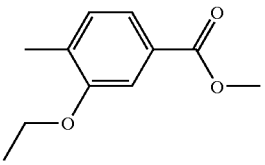 | 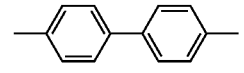 |  | |
| 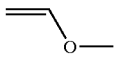 | (CH₂)₆O | 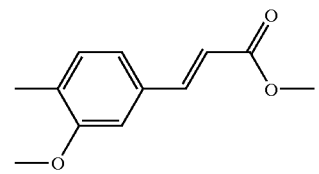 | 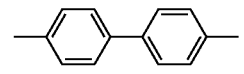 |  | |
| 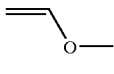 | (CH₂)₆O | 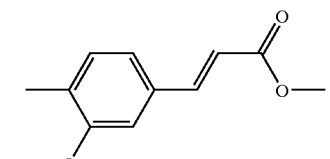 | 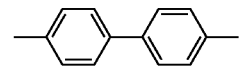 |  | M.p. (C—S_X) 86° C., S_X—I 93° C. |

-continued
| R¹ | S¹—O | A—Z¹ | B | COO—S²—R² | Phase transitions |
|---|---|---|---|---|---|
| 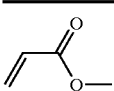 | (CH₂)₆O | 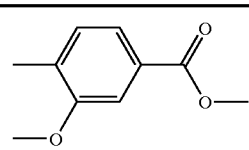 |  |  | M.p. (C—I) 66° C. |
| 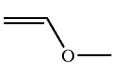 | (CH₂)₆O | 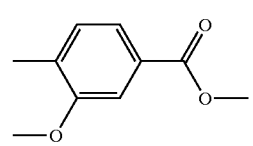 |  | 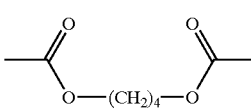 | M.p. (C—Sₓ) 64° C., Sₓ—N 77° C., N—I 83° C. |
| 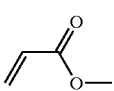 | (CH₂)₆O | 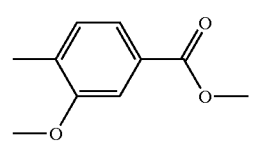 | 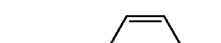 | 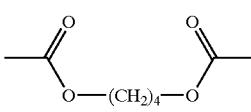 | |
| 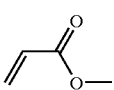 | (CH₂)₆O | 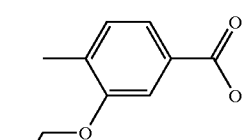 | 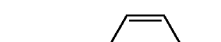 | 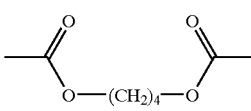 | |
| 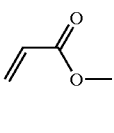 | (CH₂)₉O | 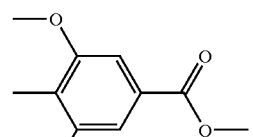 | 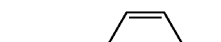 | 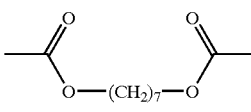 | |
| 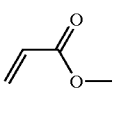 | (CH₂)₆O | 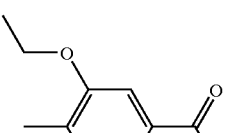 | 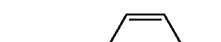 | 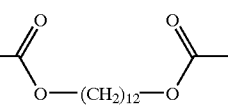 | |
| 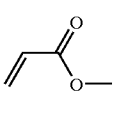 | (CH₂)₄O | 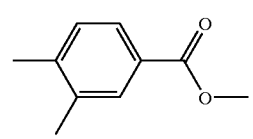 | 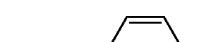 | 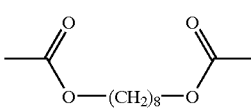 | |
| 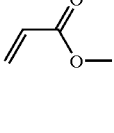 | (CH₂)₁₂O | 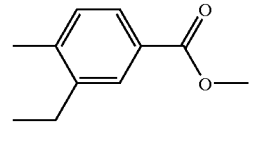 | 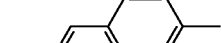 | 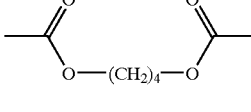 | |
| 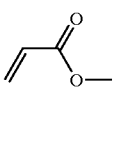 | (CH₂)₆O | 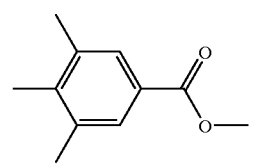 | 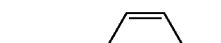 | 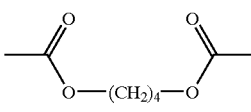 | |

-continued

| R¹ | S¹—O | A—Z¹ | B | COO—S²—R² | Phase transitions |
|---|---|---|---|---|---|
| (vinyl ether) | (CH₂)₇O | (dimethylbenzoate) | (naphthalene) | (acetate-(CH₂)₄-O-vinyl) | |
| (acrylate) | (CH₂)₆O | (methoxycinnamate) | (naphthalene) | (acetate-(CH₂)₄-O-acrylate) | |
| (acrylate) | (CH₂)₆O | (ethoxycinnamate) | (naphthalene) | (acetate-(CH₂)₄-O-acrylate) | |

EXAMPLE 2

4'-(6-Acryloyloxyhexyloxy)-3'-methoxybiphenyl-4-carboxylic Acid 4-(4-Acryloyloxybutoxycarbonyl) phenyl Ester

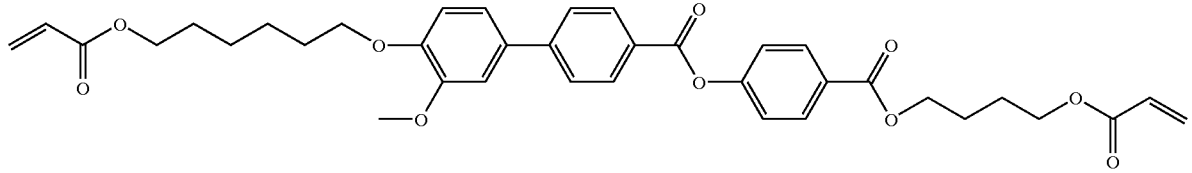

The preparation is analogous to Example 1 from 2.64 g (10 mmol) of 4-hydroxybenzoic acid 4-acryloyloxybutyl ester, 3.99 g (10 mmol) of 4'-(6-acryloyloxyhexyloxy)-3'-methoxybiphenyl-4-carboxylic acid, 0.12 g (1 mmol) of DMAP and 2.11 g (11 mmol) of EDC. Purification of the residue by chromatography on silica gel using cyclohexane/ethyl acetate (7:3) and recrystallisation once from ethanol yields 4'-(6-acryloyloxyhexyloxy)-3'-methoxybiphenyl-4-carboxylic acid 4-(4-acryloyloxybutoxycarbonyl)-phenyl ester.

The 4'-(6-acryloyloxyhexyloxy)-3'-methoxybiphenyl-4-carboxylic acid used as starting material is prepared according to a known process by palladium-catalysed boronic acid coupling of 4-bromo-2-methoxyphenol and 4-formylphenylboronic acid, subsequent Williamson etherification of the phenolic hydroxy group with acrylic acid 6-chlorohexyl ester and then oxidation of the aldehyde function to the acid (see Scheme 3).

The following compounds can be prepared in an analogous manner:

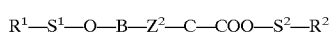

| R¹ | S¹—O | B | Z²—C | COO—S²—R² | Phase transitions |
|----|------|---|------|-----------|-------------------|

-continued

| R¹ | S¹—O | B | Z²—C | COO—S²—R² | Phase transsitions |
|---|---|---|---|---|---|
| acryloyl | (CH₂)₈O | 3-methylbiphenyl | naphthyl | —COO—(CH₂)₄—O—acryloyl | |
| acryloyl | (CH₂)₉O | 3-ethylbiphenyl | naphthyl | —COO—(CH₂)₄—O—acryloyl | |
| acryloyl | (CH₂)₆O | 3,5-bis(ethoxy)biphenyl | naphthyl | —COO—(CH₂)₁₂—O—acryloyl | |
| vinyloxy | (CH₂)₆O | 3-ethoxybiphenyl | naphthyl | —COO—(CH₂)₆—O—vinyl | |
| vinyloxy | (CH₂)₆O | 3-ethoxybiphenyl | naphthyl | —COO—(CH₂)₆—O—vinyl | |

EXAMPLE 3

4'-[4-(6-Acryloyloxyhexyloxy)-3-methoxybenzovloxy]biphenyl-4-carboxylic Acid 4-(6-Acryloyloxyhexyloxy)phenyl Ester

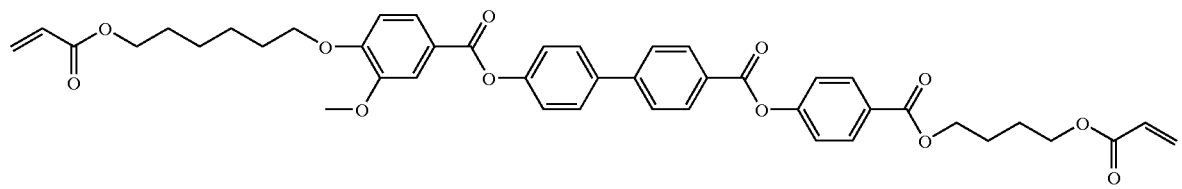

The preparation is analogous to Example 1 from 2.64 g (10 mmol) of 4-hydroxybenzoic acid 4-acryloyloxybutyl ester, 5.19 g (10 mmol) of 4'-[4-(6-acryloyloxyhexyloxy)-3-methoxybenzoyloxy]biphenyl-4-carboxylic acid, 0:12 g (1 mmol) of DMAP and 2.11 g (11 mmol) of EDC. Purification of the residue by chromatography on silica gel using cyclohexane/ethyl acetate (7:3) and recrystallisation once from ethanol yields 4'-[4-(6-acryloyloxyhexyloxy)-3-methoxybenzoyloxy]biphenyl-4-carboxylic acid 4-(6-acryloyloxyhexyloxy)phenyl ester.

The 4'-[4-(6-acryloyloxyhexyloxy)-3-methoxybenzoyloxy]biphenyl-4-carboxylic acid used as starting material is prepared as shown in Scheme 4 according to methods known to the person skilled in the art from 4-[6-acryloyloxyhexyloxy)-3-methoxybenzoic acid.

The following compounds can be prepared in analogous manner:

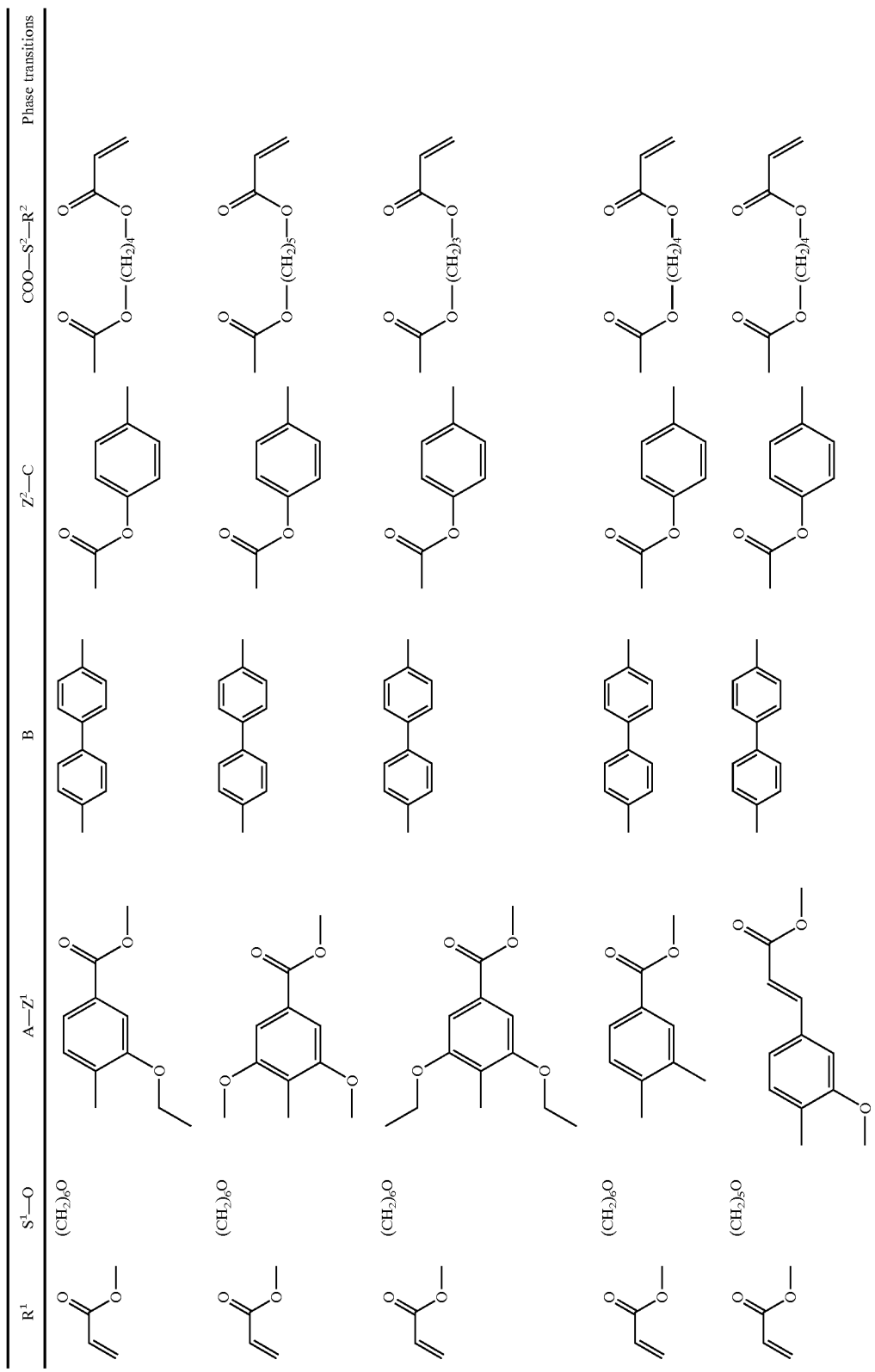

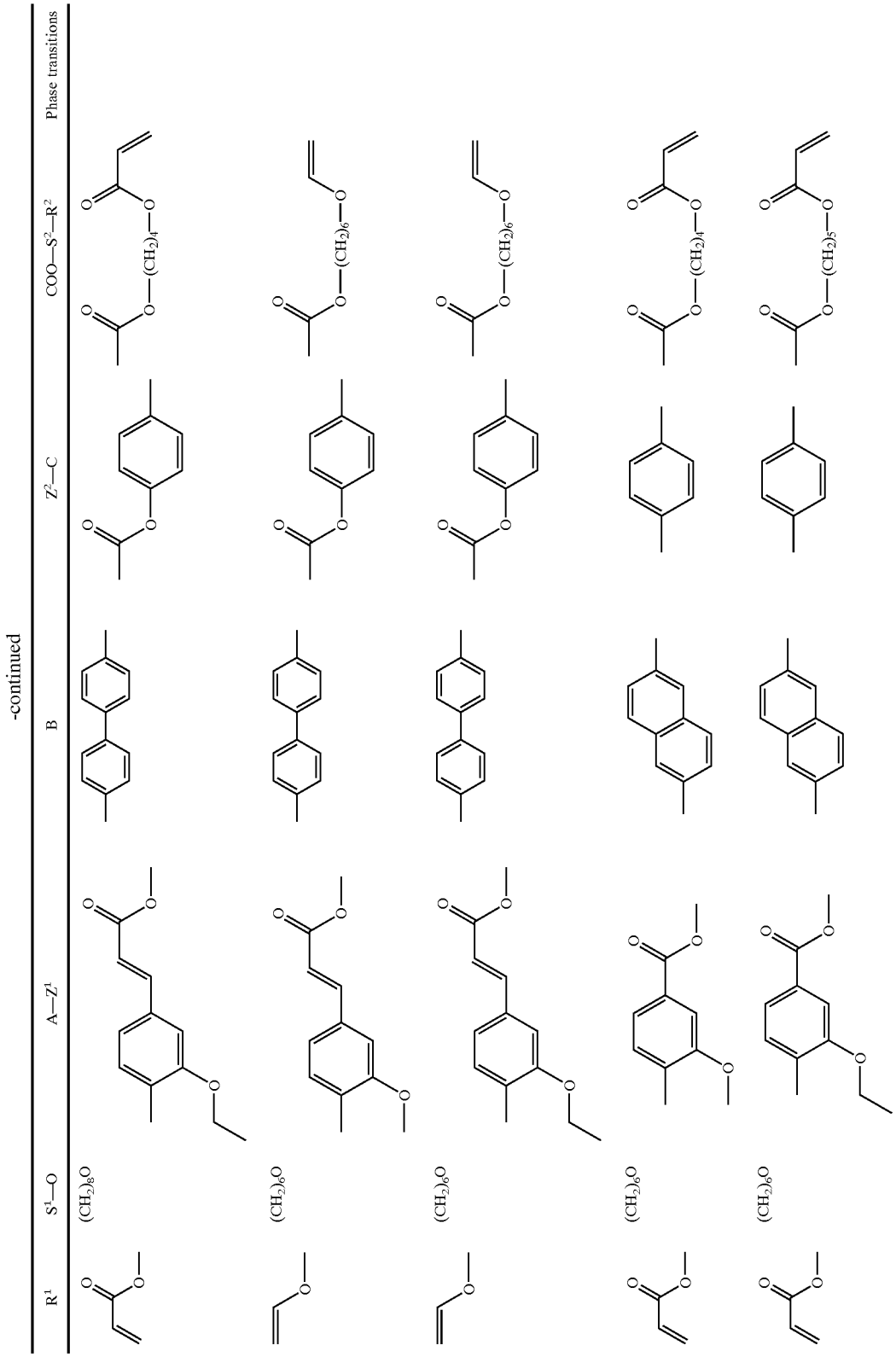

-continued
| R¹ | S¹—O | A—Z¹ | B | Z²—C | COO—S²—R² | Phase transitions |
|---|---|---|---|---|---|---|
| 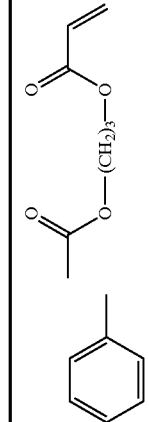 | (CH₂)₆O | 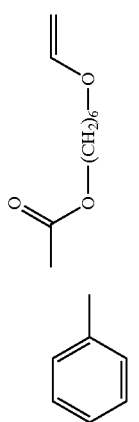 | 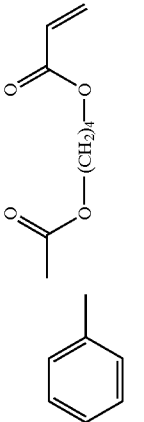 | 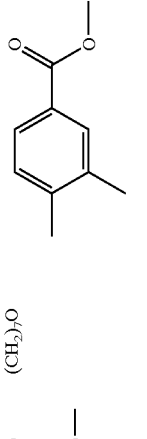 | 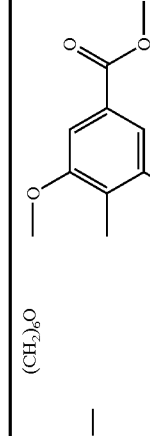 | |
| 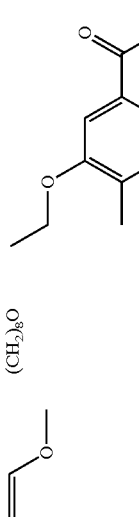 | (CH₂)₈O | 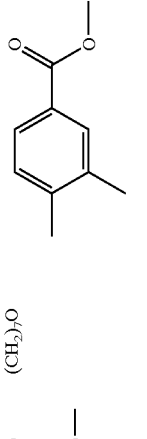 | 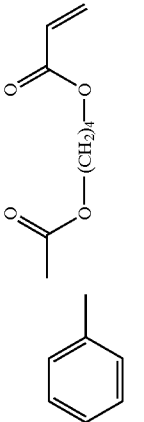 | 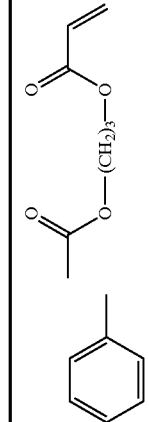 | 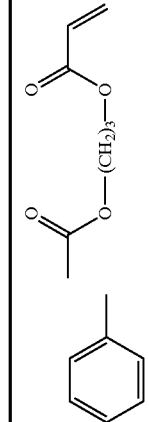 | |
| 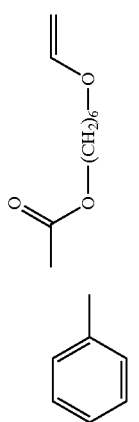 | (CH₂)₇O | 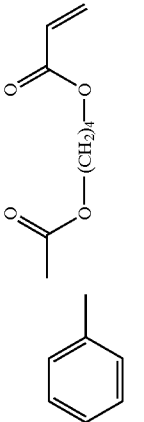 | 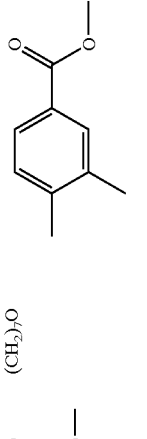 | 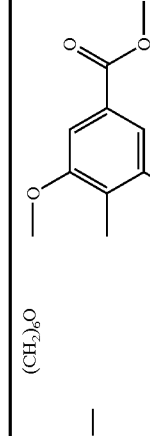 | 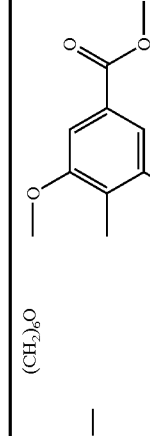 | |

-continued

| R¹ | S¹—O | A—Z¹ | B | Z²—C | COO—S²—R² | Phase transitions |
|---|---|---|---|---|---|---|

EXAMPLE 4

4'-(6-Acryloyloxyhexyloxy)-3'-methoxybiphenyl-4-carboxylic Acid 4'-(4-Acryloyloxybutoxycarbonyl)biphenyl-4-yl Ester

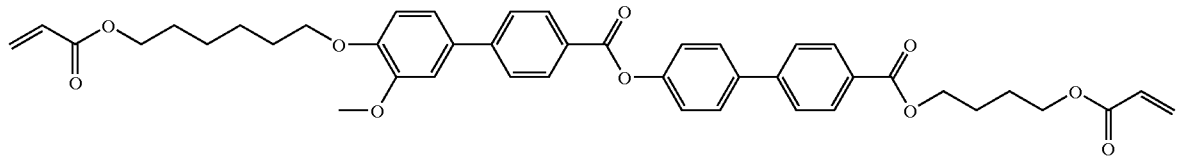

The preparation is analogous to Example 1 from 3.40 g (10 mmol) of 4'-hydroxybiphenyl-4-carboxylic acid 4-acryloylbutyl ester, 3.99 g (10 mmol) of 4'-(6-acryloyloxyhexyloxy)-3'-methoxybiphenyl-4-carboxylic acid, 0.12 g (1 mmol) of DMAP and 2.11 g (11 mmol) of EDC. Purification of the residue by chromatography on silica gel using cyclohexane/ethyl acetate (7:3) and recrystallisation once from ethanol yields 4'-(6-acryloyloxyhexyloxy)-3'-methoxybiphenyl-4-carboxylic acid 4'-(4-acryloyloxybutoxycarbonyl)-biphenyl-4-yl ester.

The following compounds can be prepared in analogous manner:

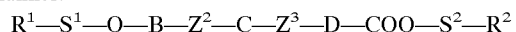

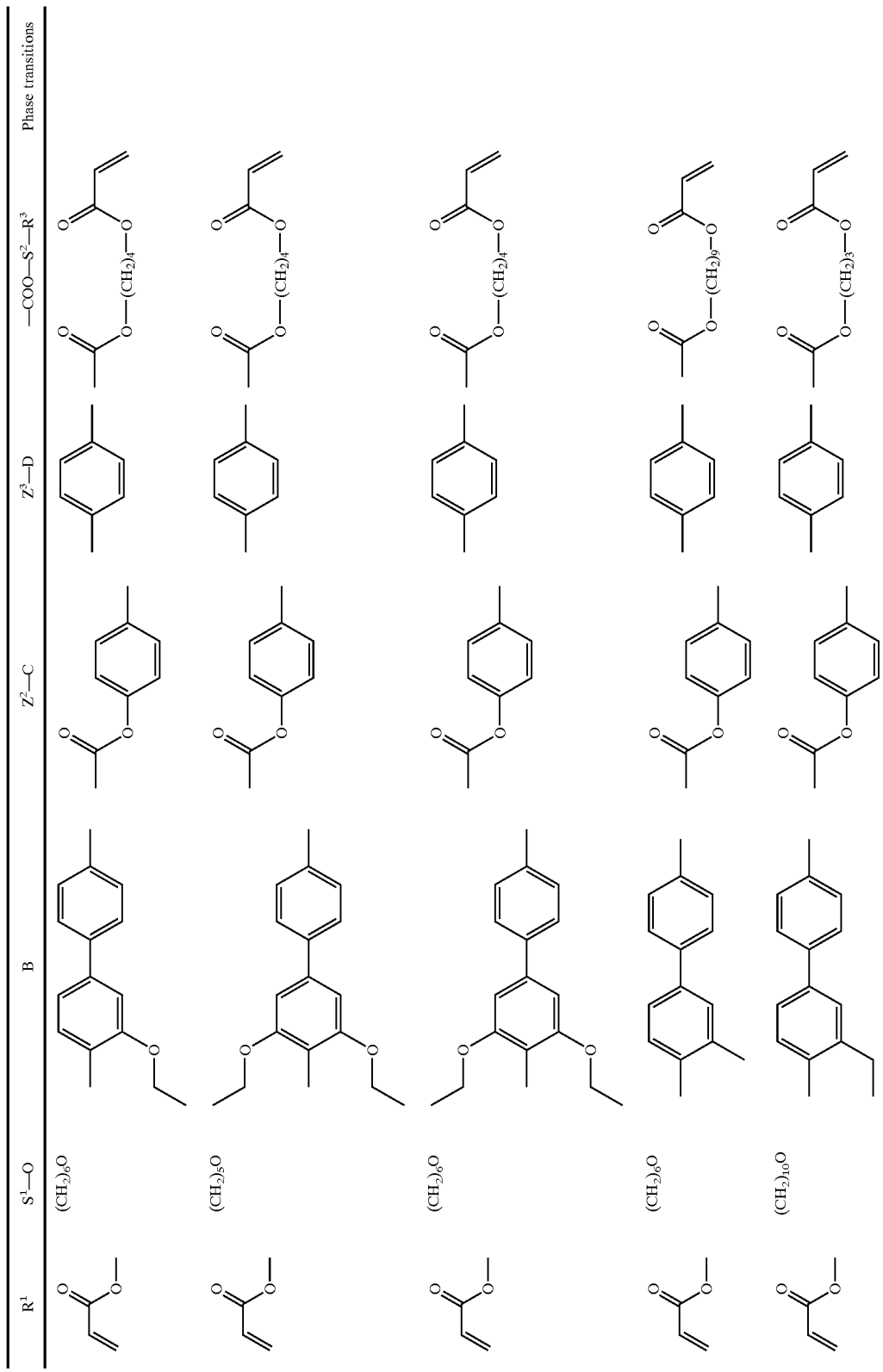

| R¹ | S¹—O | B | Z²—C | Z³—D | —COO—S²—R³ | Phase transitions |
|---|---|---|---|---|---|---|
| CH₂=CH-O- | (CH₂)₆O | 3,4,5-trimethylphenyl-phenyl | phenyl-OC(O)- | phenyl-methyl | -C(O)-O-(CH₂)₄-O-CH=CH₂ | |
| CH₂=CH-O- | (CH₂)₅O | 3,4,5-triethyl/methyl-phenyl-phenyl | phenyl-OC(O)- | phenyl-methyl | -C(O)-O-(CH₂)₆-O-CH=CH₂ | |
| CH₂=CH-C(O)-O- | (CH₂)₆O | 3-methoxy-4-methyl-phenyl-phenyl | phenyl-OC(O)- | pyridyl-methyl | -C(O)-O-(CH₂)₃-O-C(O)-CH=CH₂ | |
| CH₂=CH-C(O)-O- | (CH₂)₆O | 3-ethoxy-4-methyl-phenyl-phenyl | phenyl-OC(O)- | pyridyl-methyl | -C(O)-O-(CH₂)₅-O-C(O)-CH=CH₂ | |
| CH₂=CH-C(O)-O- | (CH₂)₆O | 3,5-dimethoxy-4-methyl-phenyl-phenyl | phenyl-OC(O)- | pyridyl-methyl | -C(O)-O-(CH₂)₄-O-C(O)-CH=CH₂ | |

-continued
| R¹ | S¹—O | B | Z²—C | Z³—D | —COO—S²—R³ | Phase transitions |
|---|---|---|---|---|---|---|
| 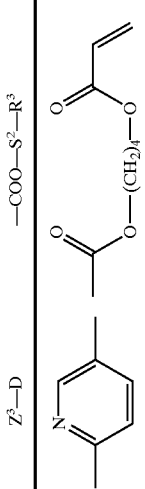 | (CH₂)₇O | 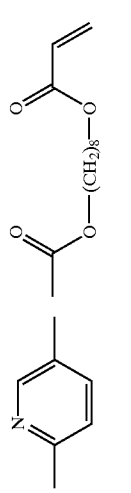 | 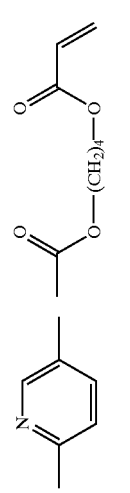 | 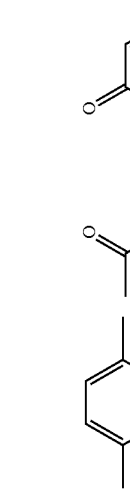 |  | |
| 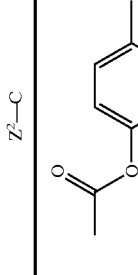 | (CH₂)₆O | 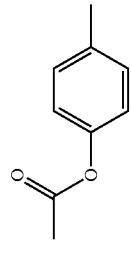 | 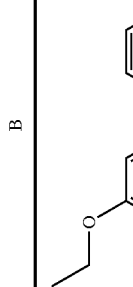 | 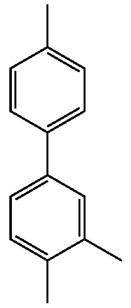 | 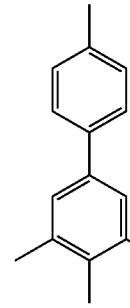 | |
| 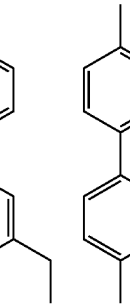 | (CH₂)₆O |  | 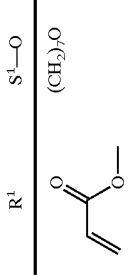 | 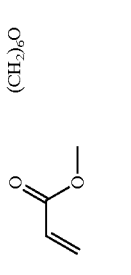 | 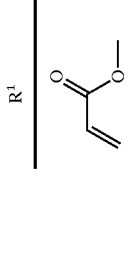 | |
| 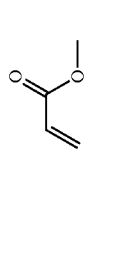 | (CH₂)₆O | 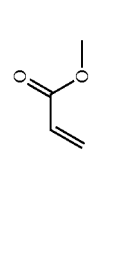 | 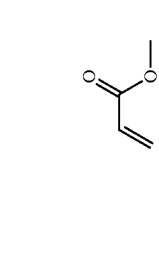 |  |  | |
|  | | | | | | |

-continued
| R¹ | S¹—O | B | Z²—C | Z³—D | —COO—S²—R³ | Phase transitions |
|---|---|---|---|---|---|---|
| 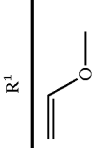 | (CH₂)₆O | 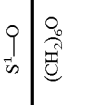 |  |  |  | |
| 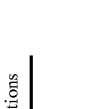 | (CH₂)₆O | 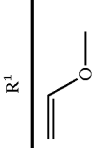 | 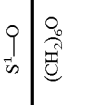 |  |  | |
|  | (CH₂)₅O | 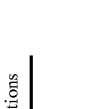 | 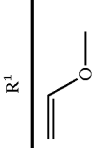 | 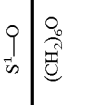 |  | |

-continued
| R¹ | S¹—O | B | Z²—C | Z³—D | —COO—S²—R³ | Phase transitions |
|---|---|---|---|---|---|---|
| 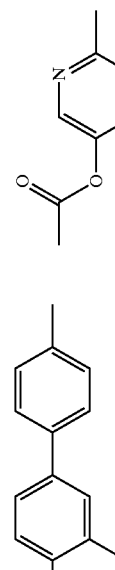 | (CH₂)₆O | 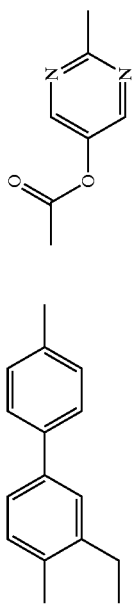 | 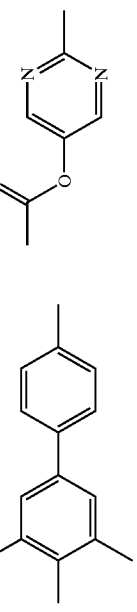 | 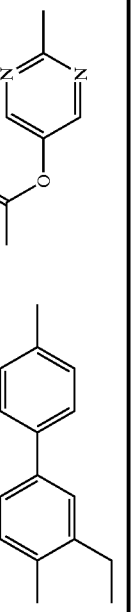 | 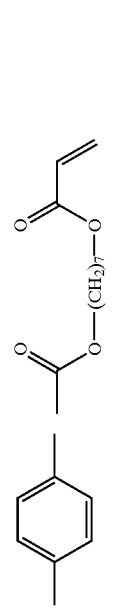 | |
| 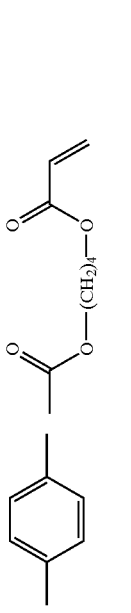 | (CH₂)₉O | 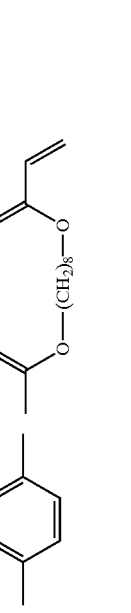 | 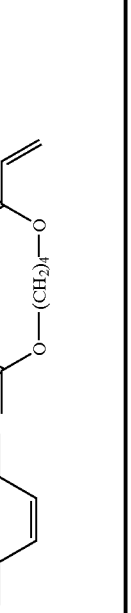 | 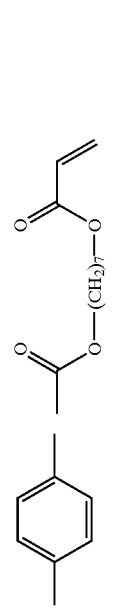 | 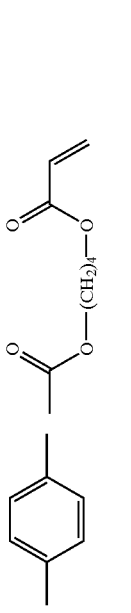 | |
| 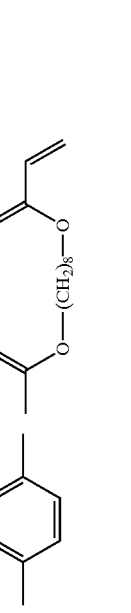 | (CH₂)₆O | 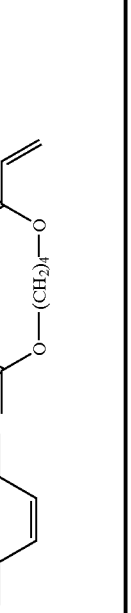 | 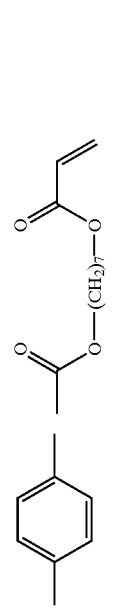 | 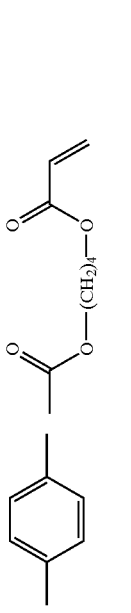 | 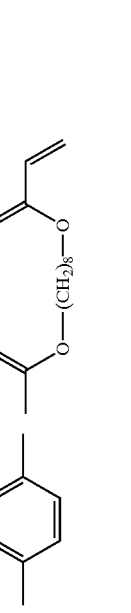 | |
| 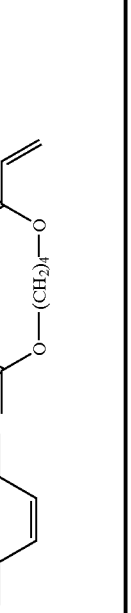 | (CH₂)₃O | 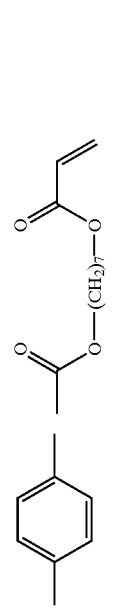 | 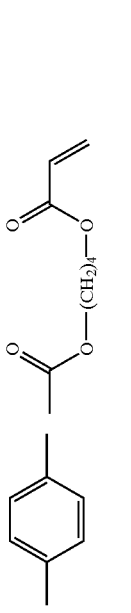 | 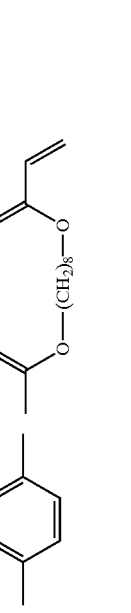 | 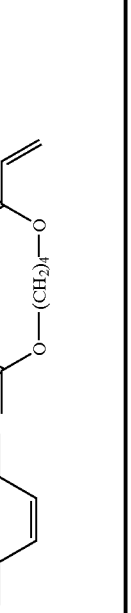 | |

EXAMPLE 5

A mixture of 40% by weight of 4'-[4-(6-acryloyloxyhexyloxy)-3-methoxybenzoyloxy]biphenyl-4-carboxylic acid 4-acryloyloxybutyl ester, 40% by weight of 4'-[4-(6-acryloyloxyhexyloxy)-3-ethoxybenzoyloxy]biphenyl-4-carboxylic acid 4-acryloyloxybutyl ester and 20% by weight of 4-(6-acryloyloxyhexyloxy)benzoic acid 4-[4-(6-acryloyloxyhexyloxy)benzoyloxy]-2-methylphenyl ester is introduced into a parallel cell. The anisotropy of that cell is Δn=0.2. The clearing point of the mixture is $T_c$=54.3° C., with a phase transition $S_A$/N being observed at 35.3° C. The mixture can be cooled to below room temperature.

What is claimed is:

1. A compound of the general formula I:

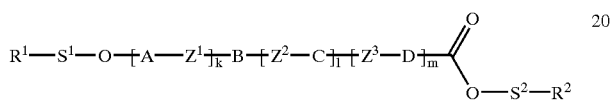

wherein $R^1$, $R^2$ each independently of the other represents a crosslinkable group;

$S^1$, $S^2$ each independently of the other represents a spacer unit;

with the proviso that $R^1$—$S^1$ and $R^2$—$S^2$ do not contain any —O—O— or —N—O— groups;

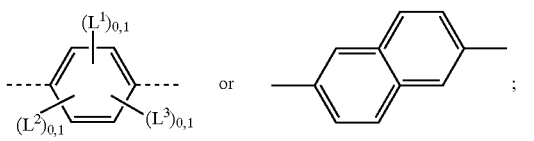

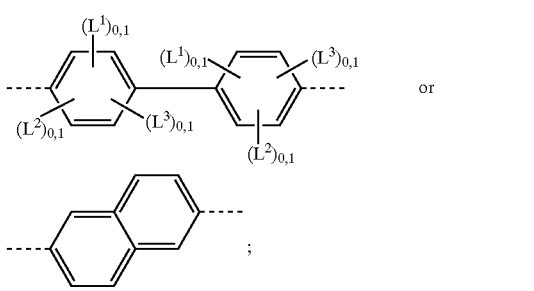

wherein also at least one of the phenylene rings in A, B, C or D may be replaced by a 1,4-phenylene ring in which one or two non-adjacent CH groups have been replaced by nitrogen; and $L^1$, $L^2$, $L^3$ each independently of the others represents hydrogen, $C_1$-$C_{20}$-alkyl, $C_2$-$C_{20}$-alkenyl, $C_1$-$C_{20}$-alkoxy, $C_2$-$C_{20}$-alkenyloxy, $C_1$-$C_{20}$-alkoxycarbonyl, formyl, $C_1$-$C_{20}$-alkylcarbonyl or $C_1$-$C_{20}$-alkylcarbonyloxy, with the proviso that in at least one phenylene ring in A, B, C or D one of the mentioned substituents is other than hydrogen;

k, l, m are 0 or 1, wherein k+l+m must be equal to 1 or 2; and $Z^1$, $Z^2$, $Z^3$ each independently of the others represents a single bond, —$CH_2CH_2$—, —$CH_2O$—, —$OCH_2$—, —COO—, —OOC—, —CH=CH—COO—, —OOC—CH=CH—, —$(CH_2)_4$—, —$(CH_2)_3$—, —$(CH_2)_3O$— or —C≡C—.

2. A compound according to claim 1 wherein $R^1$, $R^2$ each independently of the other represents $CH_2$=CH—, $CH_2$=CH—COO—, $CH_2$=C($CH_3$)—COO—, $CH_2$=C(Cl)—COO—, $CH_2$=C(Ph)—COO—, $CH_2$=CH—COO—Ph—, $CH_2$=CH—CO—NH—, $CH_2$=C($CH_3$)—CONH—, $CH_2$=C(Cl)—CONH—, $CH_2$=C(Ph)—CONH—, $CH_2$=C(COOR')—$CH_2$—COO—, (R'OOC)—$CH_2$—C=$CH_2$—COO—, $CH_2$=CH—O—, $CH_2$=CH—OOC—, CH=CH—Ph—, cis- or trans-HOO—CR'=CR'—COO—, siloxane,

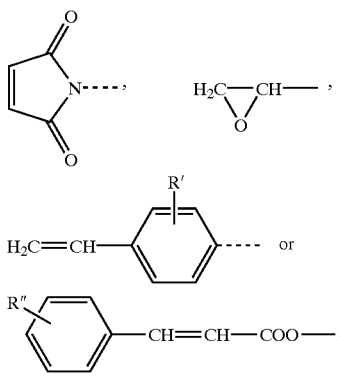

wherein (Ph) represents phenyl, Ph represents phenylene, R' represents lower alkyl and R" represents methyl, methoxy, cyano or halogen.

3. A compound according to claim 1 wherein $S^1$, $S^2$ each independently of the other represents a straight-chain or branched alkylene grouping —$(CH_2)_r$— which may optionally be mono- or poly-substituted by fluorine, or —$((CH_2)_2$—O$)_r$, or a chain of the formula —$(CH_2)_r$—Y—$(CH_2)_s$— which may optionally be mono- or poly-substituted by fluorine, wherein Y is a single bond or a linking functional group, where r and s are each an integer from 0 to 20, with the proviso that 2≦r+s≦20.

4. A compound according to claim 3 wherein

Y is a linking functional group comprising —O—, —COO—, —OOC—, —$NR^3$—, —$NR^3$—CO, —CO—$NR^3$—, —$NR^3$—COO—, —OCO—$NR^3$—, —$NR^3$—CO—$NR^3$—, —O—OC—O—, —CH=CH—, —C≡C—, wherein $R^3$ represents hydrogen or lower alkyl, or —(Si[$(CH_3)_2$]O$)_u$—, —O$(CH_2)_t$(Si)[$(CH_3)_2$]O$)_u$Si[$(CH_3)_2$]$(CH_2)_tO$— or —NH$(CH_2)_t$(Si[$CH_3)_2$]O$)_u$Si[$(CH_3)_2$]$(CH_2)_t$NH—, wherein t is an integer from 1 to 12 and u is an integer from 1 to 16, with the proviso that 2t+u≦20.

5. A compound according to claim 1 of one of formulae I-A to I-G

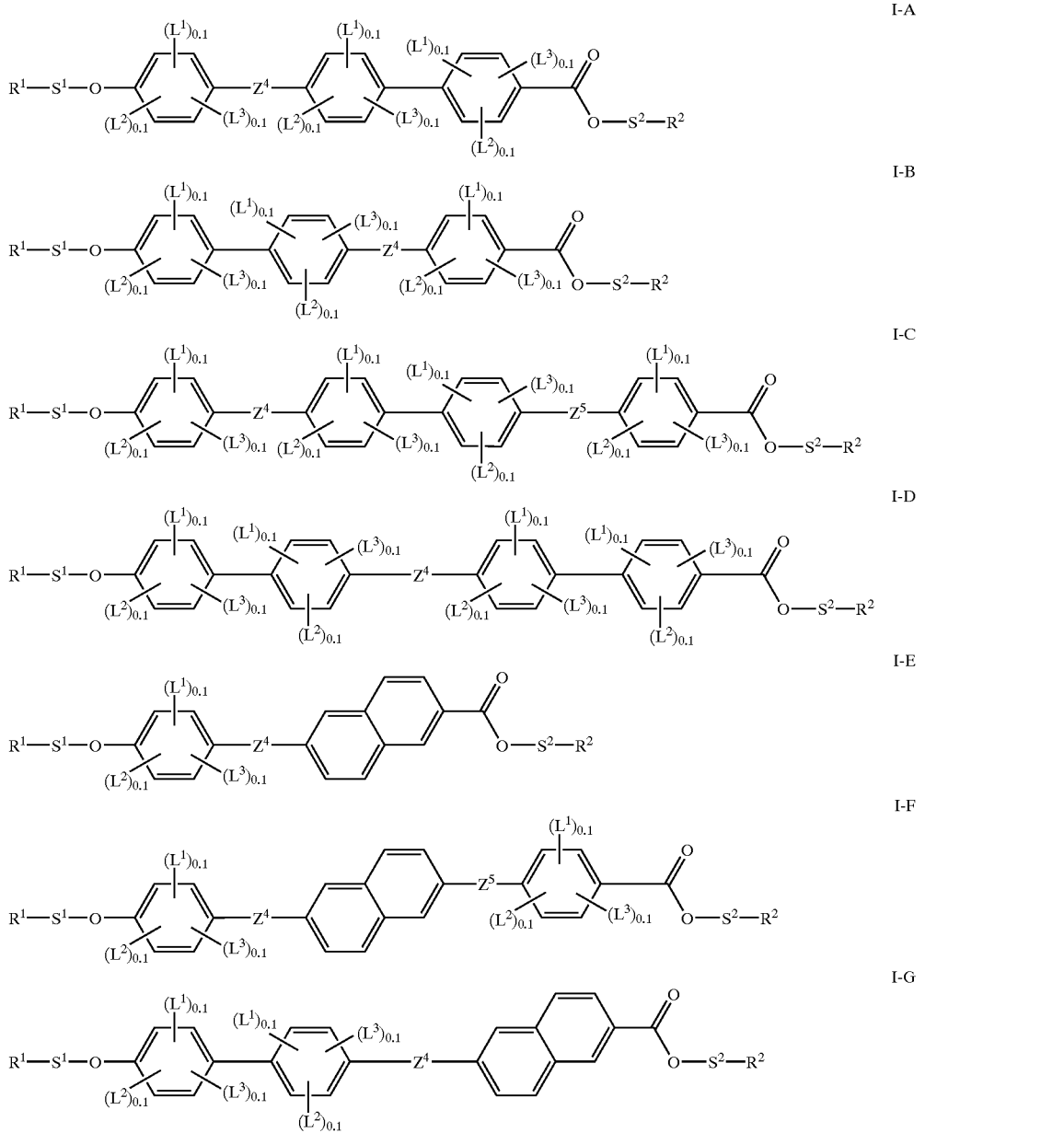

wherein

Z⁴, Z⁵ each independently of the other represents a single bond, —C≡C—, —COO— or —CH=CH—COO—; and $R^1$, $R^2$, $S^1$, $S^2$, $L^1$, $L^2$ and $L^3$ are as defined in claim 1.

6. A compound according to claim 1 of formulae I-A-1 or I-A-2

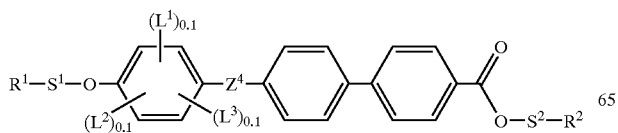

-continued

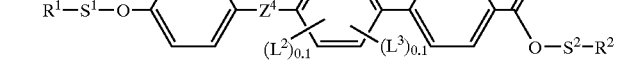

wherein $L^1$, $L^2$, $L^3$ each independently of the others represents hydrogen, $C_1$–$C_{20}$-alkyl, $C_2$–$C_{20}$-alkenyl, $C_1$–$C_{20}$-alkoxy or $C_2$–$C_{20}$-alkenyloxy, wherein at least one substituent must be other than hydrogen;

$Z^4$ represents —C≡C—, —COO—, or —CH=CH—COO—; and $R^1$, $R^2$, $S^1$ and $S^2$ are as defined in claim 1.

7. A compound according to claim 6, in which the group

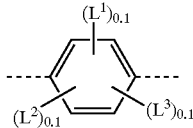

is defined by

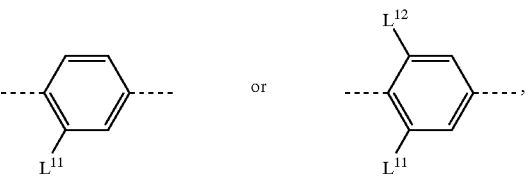

wherein $L^{11}$, $L^{12}$ each independently of the other represents $C_1$–$C_{20}$-alkyl, $C_2$–$C_{20}$-alkenyl, $C_1$–$C_{20}$-alkoxy or $C_2$–$C_{20}$-alkenyloxy.

8. A compound according to claim 6, wherein $Z^4$ represents —COO— or —CH=CH—COO—.

9. A compound according to claim 1 of formula I-F-1

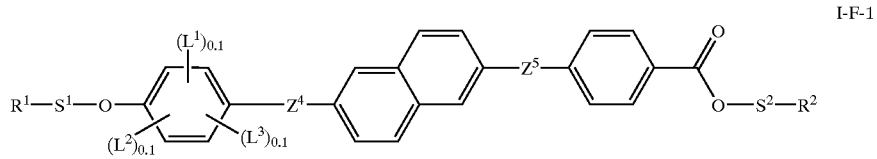

I-F-1 wherein $L^1$, $L^2$, $L^3$ each independently of the others represents hydrogen, $C_1$–$C_{20}$-alkyl, $C_2$–$C_{20}$-alkenyl, $C_1$–$C_{20}$-alkoxy or $C_2$–$C_{20}$-alkenyloxy, wherein at least one substituent must be other than hydrogen;

$Z^4$ represents —C≡C—, —COO— or —CH=CH—COO—;

$Z^5$ represents a single bond, —COO— or —CH=CH—COO—; and $R^1$, $R^2$, $S^1$ and $S^2$ are as defined in claim 1.

10. A compound according to claim 9, in which the group

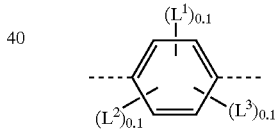

is defined by

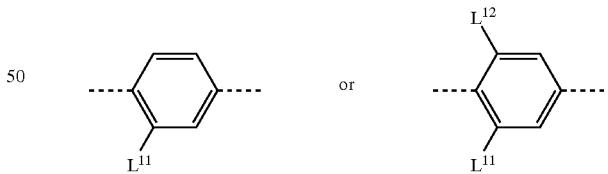

wherein $L^{11}$, $L^{12}$ each independently of the other represents $C_1$–$C_{20}$-alkyl, $C_2$–$C_{20}$-alkenyl, $C_1$–$C_{20}$-alkoxy or $C_2$–$C_{20}$-alkenyloxy.

11. An optical or electro-optical device comprising a compound according to claim 1.

12. A crosslinkable liquid crystalline mixture comprising at least two components, of which at least one component is a compound according to claim 1.

13. A crosslinkable liquid crystalline mixture according to claim 12, wherein it further comprises one or more compounds from the group of formulae

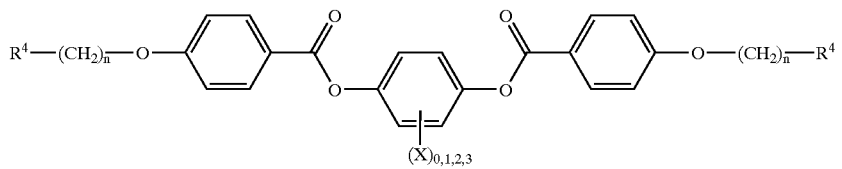
II
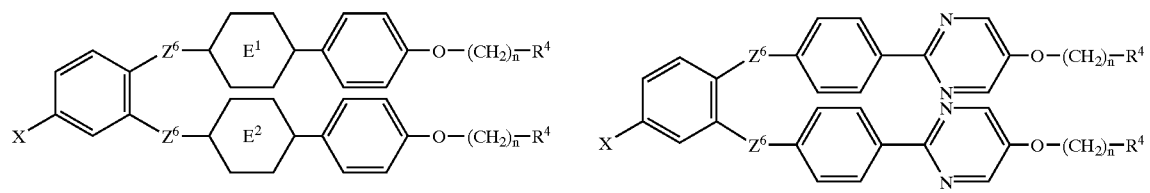
III IV
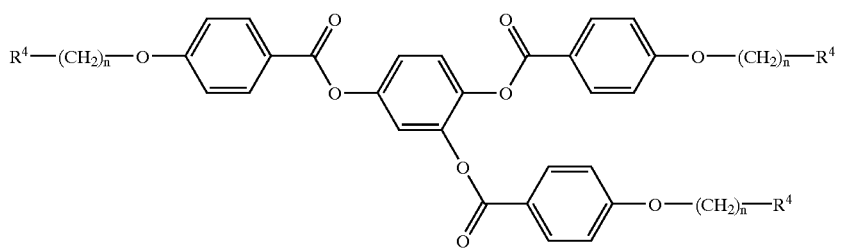
V
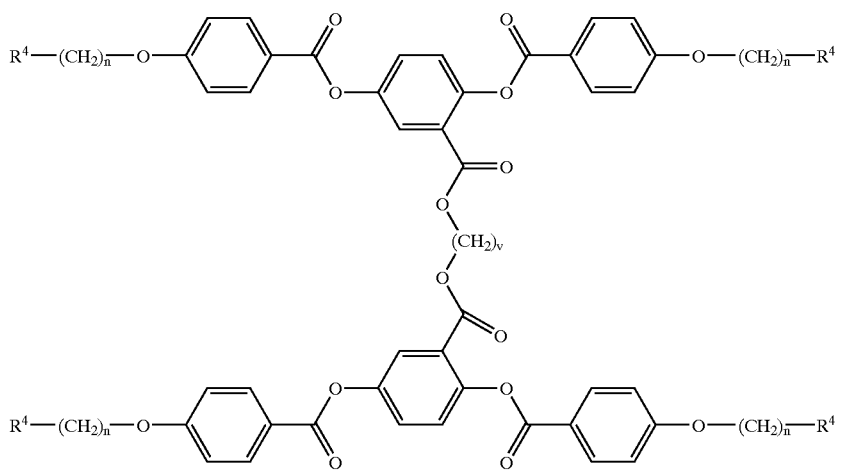
VI
VII VIII
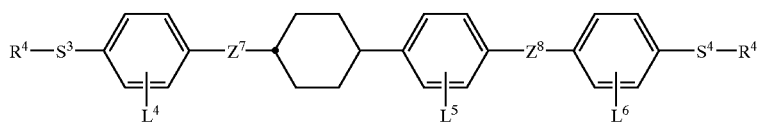
IX
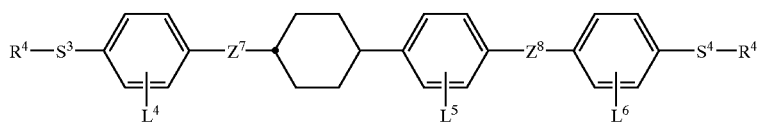

wherein $R^4$ represents a polymerisable group;

$S^3$, $S^4$ each independently of the other is —$(CH_2)_n$— or —$O(CH_2)_n$—;

$E^1$, $E^2$ each independently of the other represents 1,4-phenylene, trans-1,4-cyclohexylene, pyridine-2,5-diyl, pyrimidine-2,5-diyl or trans-1,4-cyclohexylene-1,4-phenylene;

$F^1$, $F^2$ each independently of the other represents 1,4-phenylene or 2- or 3-fluoro-1,4-phenylene;

$L^4$, $L^5$, $L^6$ each independently of the others represents hydrogen, $C_1$–$C_{20}$-alkyl, $C_2$–$C_{20}$-alkenyl, $C_1$–$C_{20}$-alkoxy, $C_1$–$C_{20}$-alkoxy-carbonyl, formyl, $C_1$–$C_{20}$-alkylcarbonyl, $C_1$–$C_{20}$-alkylcarbonyloxy, halogen, cyano or nitro;

each $Z^6$ independently of any other represents —COO—, —OOC—, —OCH$_2$—, —CH$_2$O—, —(CH$_2$)$_3$—, —OOC(CH$_2$)$_2$— or —COO(CH$_2$)$_3$—;

$Z^7$ represents a single bond, —CH$_2$CH$_2$—, —CH$_2$O—, —OCH$_2$—, —COO—, —OOC—, —(CH$_2$)$_4$—, —O(CH$_2$)$_3$, —(CH$_2$)$_3$O— or —C≡C—;

$Z^8$ represents a single bond, —CH$_2$CH$_2$—, —CH$_2$O—, —OCH$_2$—, —COO—, —OOC— or —C≡C—;

each X independently of any other(s) represents hydrogen, $C_1$–$C_{20}$-alkyl, $C_2$–$C_{20}$-alkenyl, $C_1$–$C_{20}$-alkoxy, $C_1$–$C_{20}$-alkoxycarbonyl, formyl, $C_1$–$C_{20}$-alkylcarbonyl, $C_1$–$C_{20}$-alkoxycarbonyloxy, fluorine, chlorine, bromine, cyano or nitro;

each n independently of any other(s) is an integer from 2 to 20; and v is an integer from 2 to 12.

14. A crosslinkable liquid crystalline mixture according to claim 13, wherein

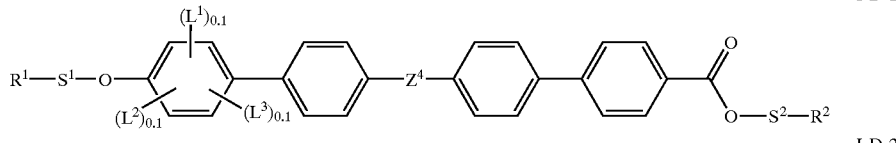

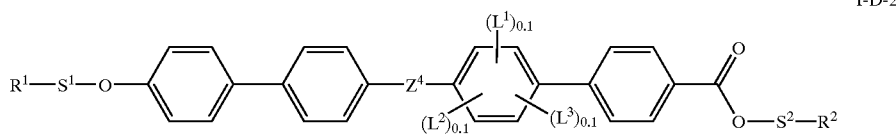

$R^4$ represents a polymerisable group comprising CH$_2$=CH—, CH$_2$=CH—O—, CH$_2$=CH—COO—, CH$_2$=C(CH$_3$)—COO—, CH$_2$=C(Cl)—COO— or

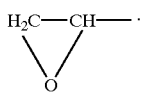

15. An optical or electro-optical device comprising a crosslinkable liquid crystalline mixture according to claim 12.

16. A compound according to claim 1 of formula I-B-1

I-B-1

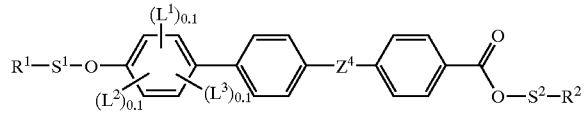

wherein $L^1$, $L^2$, $L^3$ each independently of the others represents hydrogen, $C_1$–$C_{20}$-alkyl, $C_2$–$C_{20}$-alkenyl, $C_1$–$C_{20}$-alkoxy or $C_2$–$C_{20}$-alkenyloxy, wherein at least one substituent must be other than hydrogen;

$Z^4$ represents —C≡C—, —COO—, or —CH=CH—COO—; and $R^1$, $R^2$, $S^1$ and $S^2$ are as defined in claim 1.

17. A compound according to claim 16, wherein $Z^4$ represents —COO— or —CH=CH—COO.

18. A compound according to claim 16, in which the group

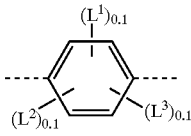

is defined by

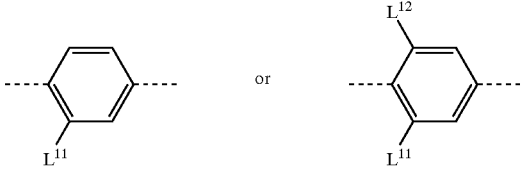

wherein $L^{11}$, $L^{12}$ each independently of the other represents $C_1$–$C_{20}$-alkyl, $C_2$–$C_{20}$-alkenyl, $C_1$–$C_{20}$-alkoxy or $C_2$–$C_{20}$-alkenyloxy.

19. A compound according to claim 1 of formulae I-D-1 or I-D-2:

I-D-1

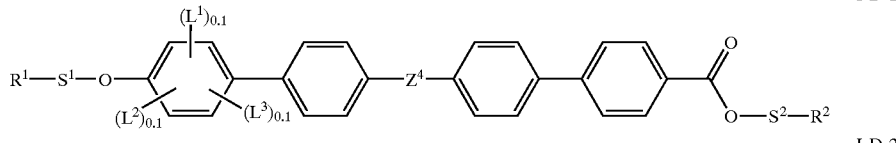

I-D-2

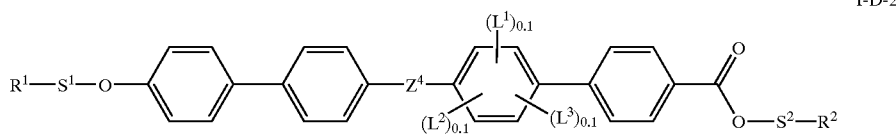

wherein $L^1$, $L^2$, $L^3$ each independently of the others represents hydrogen, $C_1$–$C_{20}$-alkyl, $C_6$–$C_{20}$-alkenyl, $C_1$–$C_{20}$-alkoxy or $C_2$–$C_{20}$-alkenyloxy, wherein at least one substituent must be other than hydrogen;

$Z^4$ represents —C≡C—, —COO— or —CH=CH—COO—; and $R^1$, $R^2$, $S^1$ and $S^2$ are as defined in claim 1.

20. A compound according to claim 19, in which the group

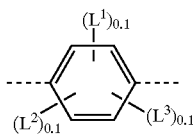

is defined by

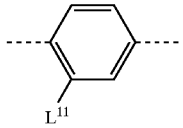 or 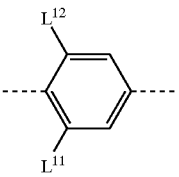

wherein $L^{11}$, $L^{12}$ each independently of the other represents $C_1$–$C_{20}$-alkyl, $C_2$–$C_{20}$-alkenyl, $C_1$–$C_{20}$-alkoxy or $C_2$–$C_{20}$-alkenyloxy.

21. A compound according to claim 1 of formula I-G-1

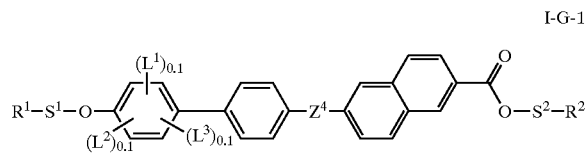

I-G-1 wherein $L^1$, $L^2$, $L^3$ each independently of the others represents hydrogen, $C_1$–$C_{20}$-alkyl, $C_2$–$C_{20}$-alkenyl, $C_1$–$C_{20}$-alkoxy or $C_2$–$C_{20}$-alkenyloxy, wherein at least one substituent must be other than hydrogen;

$Z^4$ represents —C≡C—, COO, —CH=CH—COO—; and $R^1$, $R^2$, $S^1$ and $S^2$ are as defined in claim 1.

22. A compound according to claim 21, in which the group

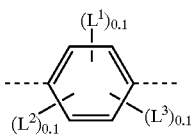

is defined by

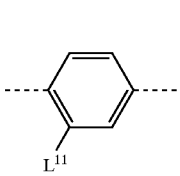 or 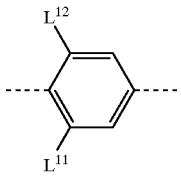

wherein $L^{11}$, $L^{12}$ each independently of the other represents $C_1$–$C_{20}$-alkyl, $C_2$–$C_{20}$-alkenyl, $C_1$–$C_{20}$-alkoxy or $C_2$–$C_{20}$-alkenyloxy.

* * * * *

UNITED STATES PATENT AND TRADEMARK OFFICE
CERTIFICATE OF CORRECTION

PATENT NO. : 6,613,245 B1
DATED : September 2, 2003
INVENTOR(S) : Angela Ohlemacher et al.

It is certified that error appears in the above-identified patent and that said Letters Patent is hereby corrected as shown below:

Title page,
Item [57], ABSTRACT,
Delete the ABSTRACT in its entirety and insert therefor --Compounds of formula (I)

wherein A, B, C and D are defined in the disclosure; k, l, m are 0 or 1, wherein $k + l + m$ equal 1 or 2; $Z^1, Z^2, Z^3$ each independently of the others represents a single bond, $-CH_2CH_2-$, $-CH_2O-$, $-OCH_2-$, $-COO-$, $-OOC-$, $-CH=CH-COO-$, $-OOC-CH=CH-$, $(CH_2)_4-$, $-O(CH_2)_3-O-$ or $-C\equiv C-$; $R^1$, $R^2$ represent crosslinkable groups, and $S^1$, $S^2$ represent spacer units.--.

Column 59,
Lines 34-38, before the first structure, insert -- A, C and D represent --.
Lines 34-47, before the structure, insert -- B represents --.

Column 60,
Line 4, "$-(CH_2)_3-$," should read -- $-O(CH_2)_3-$,--.

Column 67,
Line 24, "$-(CH_2)_3-$," should read -- $-O(CH_2)_3-$,--.

Column 68,
Line 21, "$-CH=CH-COO$." should read -- $-CH=CH-COO-$.--.

UNITED STATES PATENT AND TRADEMARK OFFICE
CERTIFICATE OF CORRECTION

PATENT NO.    : 6,613,245 B1
DATED         : September 2, 2003
INVENTOR(S)   : Angela Ohlemacher et al.

It is certified that error appears in the above-identified patent and that said Letters Patent is hereby corrected as shown below:

Column 70,
Line 6, "COO," should read -- -COO-, --.

Signed and Sealed this

Thirtieth Day of March, 2004

JON W. DUDAS
*Acting Director of the United States Patent and Trademark Office*